(12) United States Patent
Weisel et al.

(10) Patent No.: US 7,572,244 B2
(45) Date of Patent: Aug. 11, 2009

(54) MINIATURE CROSS STREAM THROMBECTOMY CATHETER

(75) Inventors: Stephen E. Weisel, Montrose, MN (US); Michael J. Bonnette, Minneapolis, MN (US); Hieu V. Le, Brooklyn Park, MN (US); Debra M. Kozak, Forest Lake, MN (US)

(73) Assignee: MEDRAD, Inc., Indianola, PA (US)

( * ) Notice: Subject to any disclaimer, the term of this patent is extended or adjusted under 35 U.S.C. 154(b) by 540 days.

(21) Appl. No.: 10/910,108

(22) Filed: Aug. 2, 2004

(65) Prior Publication Data

US 2008/0275383 A1 Nov. 6, 2008

(51) Int. Cl.
*A61M 1/00* (2006.01)
(52) U.S. Cl. .................... 604/27; 604/93.01
(58) Field of Classification Search ............... 604/246, 604/27, 35, 43–45, 93.01, 118–119, 158; 606/159, 167–168
See application file for complete search history.

(56) References Cited

U.S. PATENT DOCUMENTS

| | | | |
|---|---|---|---|
| 1,902,418 A | 3/1933 | Pilgrim |
| 3,752,617 A | 8/1973 | Burlis et al. |
| 3,930,505 A | 1/1976 | Wallach |
| 4,224,943 A | 9/1980 | Johnson et al. |
| 4,248,234 A | 2/1981 | Assenza et al. |
| 4,328,811 A | 5/1982 | Fogarty |
| 4,385,635 A | 5/1983 | Ruiz |
| 4,631,052 A | 12/1986 | Kensey |
| 4,636,346 A | 1/1987 | Gold et al. |
| 4,690,672 A | 9/1987 | Veltrup |
| 4,739,768 A | 4/1988 | Engelson |
| 4,747,405 A | 5/1988 | Leckrone |
| 4,781,186 A | 11/1988 | Simpson et al. |
| 4,782,834 A | 11/1988 | Maguire et al. |
| 4,790,813 A | 12/1988 | Kensey |
| 4,842,579 A | 6/1989 | Shiber |
| 4,883,459 A | 11/1989 | Calderon |
| 4,888,146 A | 12/1989 | Dandeneau |
| 4,898,574 A | 2/1990 | Uchiyama et al. |
| 4,898,591 A | 2/1990 | Jang et al. |
| 4,902,276 A | 2/1990 | Zakko |
| 4,913,698 A | 4/1990 | Ito et al. |
| 4,950,238 A | 8/1990 | Sullivan |

(Continued)

FOREIGN PATENT DOCUMENTS

DE 3705339 9/1988

(Continued)

*Primary Examiner*—Nicholas D Lucchesi
*Assistant Examiner*—Theodore J Stigell
(74) *Attorney, Agent, or Firm*—David Schramm; Gregory Bradley

(57) ABSTRACT

A miniature cross stream thrombectomy catheter useful in small blood vessel thrombectomy procedures. An annulus near the distal end of the miniature cross stream thrombectomy catheter is formed between a hypo-tube and a proximally directed bore of a concentrically aligned flow director whereby jet orifices in the hypo-tube communicate with the annulus to direct jet flows of saline or other fluid around and about the annulus and to be directed proximally from the annulus to pass through one or more outflow orifices and thence to pass through one or more inflow orifices thereby creating an ablation flow therebetween which loosens and carries away thrombotic materials from the walls of a blood vessel.

15 Claims, 18 Drawing Sheets

U.S. PATENT DOCUMENTS

| | | | |
|---|---|---|---|
| 5,085,649 A | 2/1992 | Flynn | |
| 5,086,842 A | 2/1992 | Cholet | |
| 5,092,873 A | 3/1992 | Simpson et al. | |
| 5,114,399 A | 5/1992 | Kovalcheck | |
| 5,135,482 A | 8/1992 | Neracher | |
| 5,163,431 A | 11/1992 | Griep | |
| 5,215,614 A | 6/1993 | Wijkamp | |
| 5,221,270 A | 6/1993 | Parker | |
| 5,234,416 A | 8/1993 | Macaulay et al. | |
| 5,250,059 A | 10/1993 | Andreas et al. | |
| 5,254,107 A | 10/1993 | Soltesz | |
| 5,259,842 A | 11/1993 | Plechinger et al. | |
| 5,273,526 A | 12/1993 | Dance et al. | |
| 5,300,022 A | 4/1994 | Klapper et al. | |
| 5,308,342 A | 5/1994 | Sepetka et al. | |
| 5,318,518 A | 6/1994 | Plechinger et al. | |
| 5,320,599 A | 6/1994 | Griep et al. | |
| 5,324,285 A | 6/1994 | Cannon | |
| 5,342,386 A | 8/1994 | Trotta | |
| 5,358,485 A | 10/1994 | Vance et al. | |
| 5,370,609 A | 12/1994 | Drasler et al. | |
| 5,372,601 A | 12/1994 | Lary | |
| 5,380,307 A | 1/1995 | Chee et al. | |
| 5,399,164 A | 3/1995 | Snoke et al. | |
| 5,425,723 A | 6/1995 | Wang | |
| 5,456,674 A | 10/1995 | Bos et al. | |
| 5,478,330 A | 12/1995 | Imran et al. | |
| 5,496,267 A | 3/1996 | Drasler et al. | |
| 5,496,294 A | 3/1996 | Hergenrother et al. | |
| 5,499,973 A | 3/1996 | Saab | |
| 5,531,685 A | 7/1996 | Hemmer et al. | |
| 5,536,242 A | 7/1996 | Willard et al. | |
| 5,542,924 A | 8/1996 | Snoke et al. | |
| 5,554,121 A | 9/1996 | Ainsworth et al. | |
| 5,571,094 A | 11/1996 | Sirhan | |
| 5,599,325 A | 2/1997 | Ju et al. | |
| 5,624,397 A | 4/1997 | Snoke et al. | |
| 5,634,897 A | 6/1997 | Dance et al. | |
| 5,658,263 A | 8/1997 | Dang et al. | |
| 5,662,622 A | 9/1997 | Gore et al. | |
| 5,676,659 A | 10/1997 | McGurk | |
| 5,681,336 A | 10/1997 | Clement et al. | |
| 5,683,345 A | 11/1997 | Waksman et al. | |
| 5,687,714 A | 11/1997 | Kolobow et al. | |
| 5,702,439 A | 12/1997 | Euteneuer et al. | |
| 5,704,926 A | 1/1998 | Sutton | |
| 5,713,849 A | 2/1998 | Bosma et al. | |
| 5,785,675 A | 7/1998 | Drasler et al. | |
| 5,792,167 A | 8/1998 | Kablik et al. | |
| 5,928,186 A | 7/1999 | Homsma et al. | |
| 5,944,686 A | 8/1999 | Patterson et al. | |
| 5,964,223 A | 10/1999 | Baran | |
| 5,976,120 A | 11/1999 | Chow et al. | |
| 5,989,210 A | 11/1999 | Morris et al. | |
| 5,989,271 A | 11/1999 | Bonnette et al. | |
| 5,997,558 A | 12/1999 | Nash | |
| 6,001,078 A | 12/1999 | Reekers | |
| 6,022,336 A | 2/2000 | Zadno-Azizi et al. | |
| 6,024,729 A | 2/2000 | Dehdashtian et al. | |
| 6,030,369 A | 2/2000 | Engelson et al. | |
| 6,045,547 A | 4/2000 | Ren et al. | |
| 6,063,069 A | 5/2000 | Cragg et al. | |
| 6,096,001 A | 8/2000 | Drasler et al. | |
| 6,117,150 A | 9/2000 | Pingleton et al. | |
| 6,128,799 A | 10/2000 | Nagata et al. | |
| 6,129,697 A | 10/2000 | Drasler et al. | |
| 6,129,698 A | 10/2000 | Beck | |
| 6,135,977 A | 10/2000 | Drasler et al. | |
| 6,224,570 B1 * | 5/2001 | Le et al. | 604/165.02 |
| 6,224,579 B1 * | 5/2001 | Modak et al. | 604/265 |
| 6,258,061 B1 | 7/2001 | Drasler et al. | |
| 6,287,280 B1 | 9/2001 | Lampropoulos et al. | |
| 6,331,176 B1 | 12/2001 | Becker et al. | |
| 6,355,027 B1 | 3/2002 | Le et al. | |
| 6,357,635 B1 | 3/2002 | Pagliaro et al. | |
| 6,375,635 B1 | 4/2002 | Moutafis et al. | |
| 6,409,863 B1 | 6/2002 | Prindle et al. | |
| 6,471,683 B2 | 10/2002 | Drasler et al. | |
| 6,544,209 B1 | 4/2003 | Drasler et al. | |
| 6,558,366 B1 | 5/2003 | Drasler et al. | |
| 6,592,549 B2 | 7/2003 | Gerdts et al. | |
| 6,676,627 B1 | 1/2004 | Bonnette et al. | |
| 6,676,637 B1 * | 1/2004 | Bonnette et al. | 604/165.02 |
| 6,719,718 B2 | 4/2004 | Bonnette et al. | |
| 6,755,803 B1 | 6/2004 | Le et al. | |
| 6,764,483 B1 | 7/2004 | Bonnette et al. | |
| 6,926,726 B2 | 8/2005 | Drasler et al. | |
| 6,945,951 B1 | 9/2005 | Bonnette et al. | |
| 2001/0051811 A1 | 12/2001 | Bonnette et al. | |
| 2003/0127620 A1 | 7/2003 | Houde | |
| 2004/0068248 A1 | 4/2004 | Mooney et al. | |
| 2004/0133264 A1 | 7/2004 | Moore | |
| 2004/0143312 A1 | 7/2004 | Samson et al. | |

FOREIGN PATENT DOCUMENTS

| | | |
|---|---|---|
| DE | 3421390 | 6/1994 |
| EP | 0251512 | 1/1988 |
| EP | 0232678 | 8/1992 |
| EP | 0528181 | 2/1993 |
| GB | 1571459 | 7/1980 |
| WO | WO9005493 | 5/1990 |
| WO | WO9410917 | 5/1994 |

* cited by examiner

MINIATURE CROSS STREAM THROMBECTOMY CATHETER

CROSS REFERENCES TO RELATED APPLICATIONS

None.

BACKGROUND OF THE INVENTION

1. Field of the Invention

The present invention is for a thrombectomy catheter, and more particularly, relates to a miniature cross stream thrombectomy catheter.

2. Description of the Prior Art

Prior art thrombectomy catheters, while being effective in many uses and situations, were fashioned of complex geometrical component configurations involving multiple components to ablate thrombus and other materials in the vasculature. Often, thrombectomy devices, due to the complexity and multiple component structure, exhibited a profile of a bulky nature which could not be accommodated by all vascular regions, such as vessels extending into the brain, which are of smaller size than vessels found in other regions of the body. Also, vessels in the brain, being of smaller proportion, have vessel walls which are thinner and more delicate than the walls of larger vessels and, therefore, require greater care when removing thrombus, lesions, plaque, and the like from the interior of the vessel. Excess ablation fluid medium velocity can be detrimental to the thin vessel walls, such as those found in the brain, where damage, such as vessel wall perforation, could occur. Other difficulties encountered with prior art thrombectomy catheters are related to the fashioning thereof where producing small components is difficult to accomplish and, as such, can prove expensive to manufacture. Especially difficult to produce is an emanator loop with rearwardly facing jet orifices and other like components which are located at the distal portion of some prior art thrombectomy catheters. Clearly what is needed is a miniature cross stream thrombectomy catheter for deployment into small vessels which can minimize vessel damage and which can be easily and affordably produced, such as is provided by the present invention.

SUMMARY OF THE INVENTION

The general purpose of the present invention is to provide a miniature cross stream thrombectomy catheter for use in small vascular regions. One embodiment of the instant invention involves a miniature cross stream thrombectomy catheter having a flexible exhaust tube having at the distal region thereof an outflow orifice and an inflow orifice extending through the wall of the exhaust tube in communication with the lumen of the exhaust tube, a flow director having a proximal bore continuous with a distal bore, such flow director being located at the distal region of the exhaust tube, a hypo-tube, also known as a high pressure tube, extending distally from the proximal end of the exhaust tube to pass through and extend a short distance beyond the distal end of the exhaust tube and to pass through and extend a short distance beyond the distal end of the distal end of the co-located flow director, one or more jet orifices located near the distal end of the hypo-tube, an annulus formed between the proximal flow director bore and the hypo-tube in the region of the jet orifices where the jet orifices provide a path of communication between the hypo-tube lumen and the annulus, a plug engaging the extended end portion of the hypo-tube, and a flexible tip attached to and extending distally from the plug. The miniature cross stream thrombectomy catheter is inserted into the vascular system and advanced to the site of thrombus, or alternately to the site of plaque or a lesion. High pressure fluid medium, such as, but not limited to, saline, is introduced, as known in the art, into the lumen of the hypo-tube and forced through the jet orifices to produce fluid jets of sufficient and nominal velocity, which are introduced into the annulus and influenced by the flow director and other factors to be directed proximally along and about the region of the exhaust tube lumen between the outer surface of the hypo-tube and the inner surface of the exhaust tube. A circulatory fluid flow where the rearwardly directed fluid jets pass is established through the outflow orifice and, thence, toward the low pressure area at the inflow orifice to impinge, loosen and break loose particles of thrombotic deposits on the wall of a blood vessel. The fluid jets and entrained thrombus flow into the relatively low pressure inflow orifice where particles of entrained thrombus are macerated by fluid jets emanating from the annulus and either removed through the lumen of the exhaust tube or recycled about the circulatory fluid flow for additional maceration. Alternatively, an insert can be included in the region of the annulus to create a fluid jet flow velocity greater than a nominal velocity if greater ablation forces are required and/or if greater thrombotic particulate removal is required. Another alternative embodiment includes a miniature cross stream thrombectomy catheter having multiple stages of outflow and inflow orifices, and another alternative embodiment includes a miniature cross stream thrombectomy catheter which can be used over and about a guidewire.

According to one embodiment of the present invention, there is provided a miniature cross stream thrombectomy catheter, including a flexible exhaust tube having an outflow orifice and an inflow orifice extending through the flexible exhaust tube wall in communication with a lumen of the flexible exhaust tube, a multiple bore flow director aligned within the distal end of the flexible exhaust tube, a hypo-tube closely fitted within one bore of the flow director extending proximally through and along the exhaust tube lumen, an annulus between another of the flow director bores and the hypo-tube, opposed jet orifices extending through the wall of the hypo-tube in communication with a hypo-tube lumen and the annulus, a plug in the distal end of the hypo-tube, and a flexible tip extending from the plug.

One significant aspect and feature of the present invention, a miniature cross stream thrombectomy catheter, is a device which can be incorporated into use within small blood vessels.

Another significant aspect and feature of the present invention is a miniature cross stream thrombectomy catheter which minimizes vessel damage by the use of a nominal fluid jet flow velocity.

Still another significant aspect and feature of the present invention is a miniature cross stream thrombectomy catheter which incorporates a flow director having a circular annulus which redirects fluid jet flow proximally and entrains fluid in through an inflow orifice and drives flow out through an outflow orifice and causing in the vessel a flow outside the catheter in a distal direction between an outflow orifice and an inflow orifice to create a flow which can recirculate and which impinges and breaks up thrombotic material Yet another significant aspect and feature of the present invention is a miniature cross stream thrombectomy catheter having proximally directed jet flow where loosened thrombus is reintroduced into the path of fluid jets for maceration.

A further significant aspect and feature of the present invention is a miniature cross stream thrombectomy catheter as found in alternative embodiments which includes the use of an insert to create increased velocity fluid jet flow of greater than nominal jet flow for increased ablation action and increased particle evacuation.

A still further significant aspect and feature of the present invention is a miniature cross stream thrombectomy catheter having multiple annulus structure where one annulus structure provides for thrombus ablation at a nominal rate and where another annulus structure provides for increased evacuation of thrombotic particles.

A still further significant aspect and feature of the present invention is a miniature cross stream thrombectomy catheter as found in alternative embodiments which includes the use of a dual wall hypo-tube having a central passageway for use over and about a guidewire.

Having thus briefly described embodiments of the present invention and having mentioned some significant aspects and features of the present invention, it is the principal object of the present invention to provide a miniature cross stream thrombectomy catheter.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
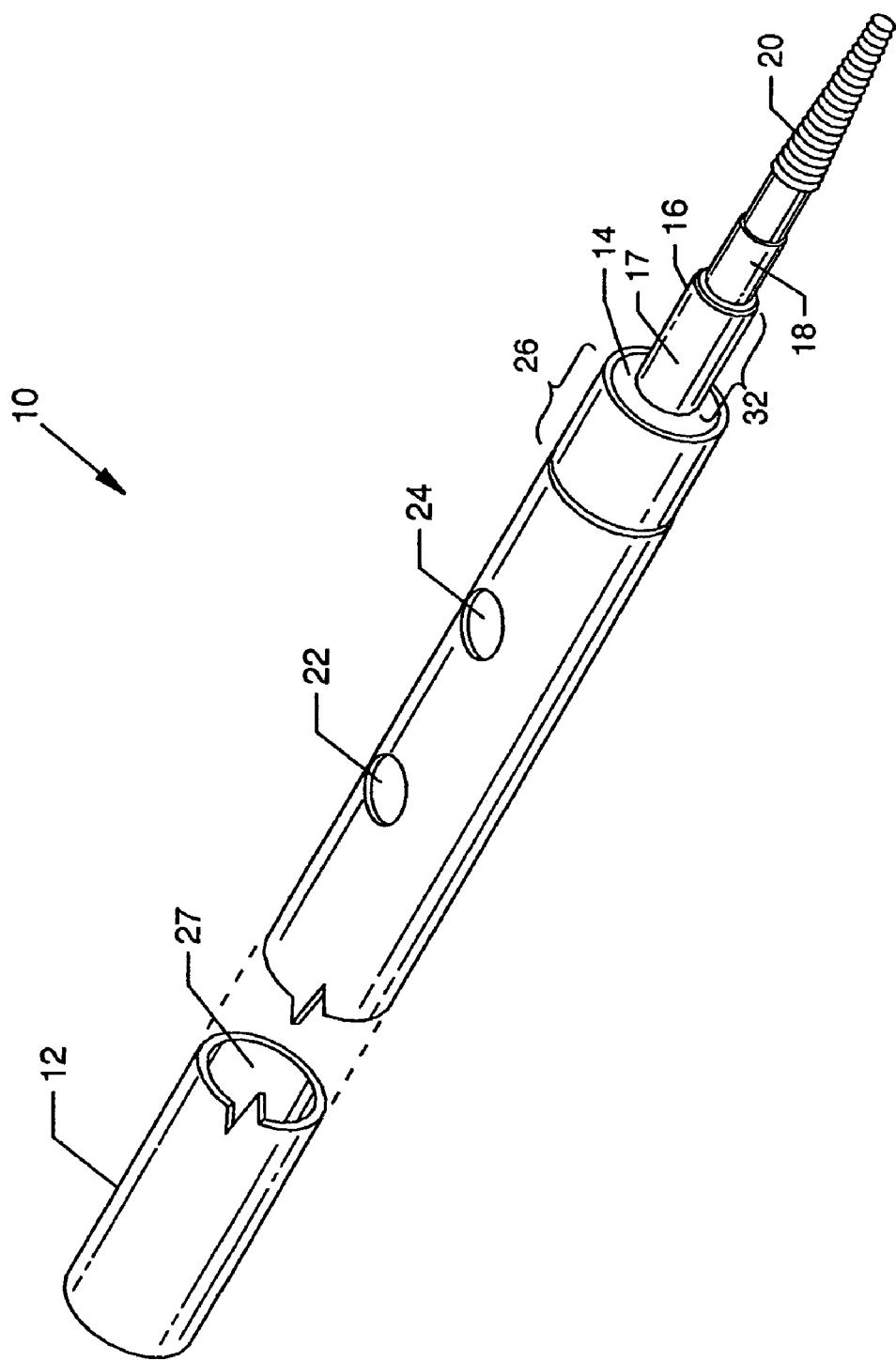
FIG. 1 is a foreshortened isometric view of a miniature cross stream thrombectomy catheter, a first embodiment of the present invention.

FIG. 1 is a foreshortened isometric view of a miniature cross stream thrombectomy catheter 9, a first embodiment of the present invention. Readily discernable major and other components visible in the illustration include a flexible exhaust tube 12 preferably of a suitable and flexible plastic or other material, a flow director 14 preferably concentrically aligned within a distal portion of the exhaust tube 12, a hypo-tube 16 aligned preferably concentrically to and extending a short distance in a distal direction beyond the distal ends of the flow director 14 and the exhaust tube 12, a plug 18, a crimp 26 at the distal end of the exhaust tube 12, and a flexible tip 20 secured about and extending from the plug 18. Also visible is an outflow orifice 22 and an inflow orifice 24 extending through the distal region of the exhaust tube 12. More than one outflow orifice 22 and more than one inflow orifice 24 can be utilized as required. The distally located crimp 26 visible at the distal end of the exhaust tube 12 causes frictional and mutual engagement and sealing of the distal regions of the exhaust tube 12, the flow director 14, and the hypo-tube 16 by compression thereof, as best viewed in FIG. 4.

Figure 2:
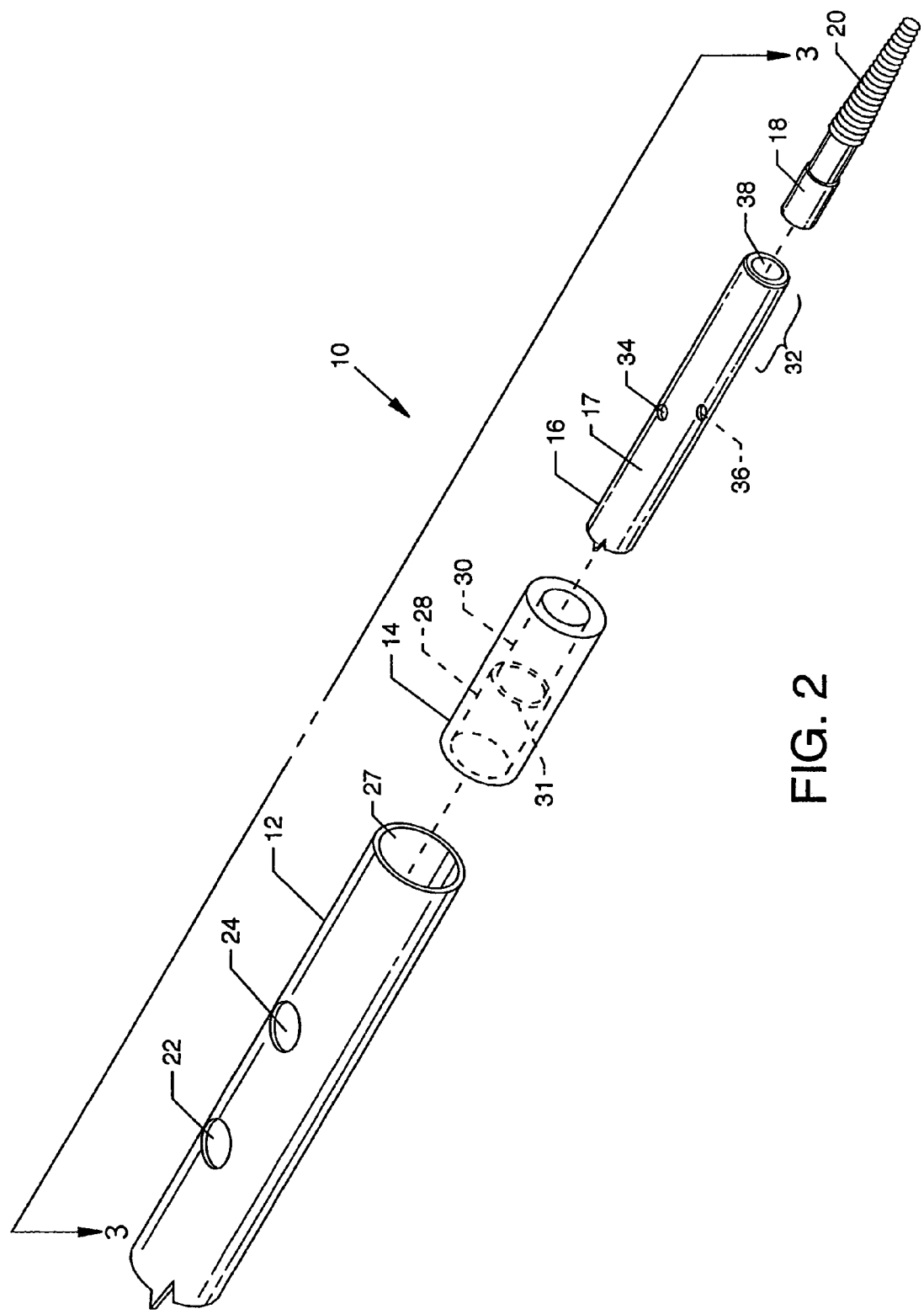
FIG. 2 is an exploded isometric view of the miniature cross stream thrombectomy catheter.
Figure 3:
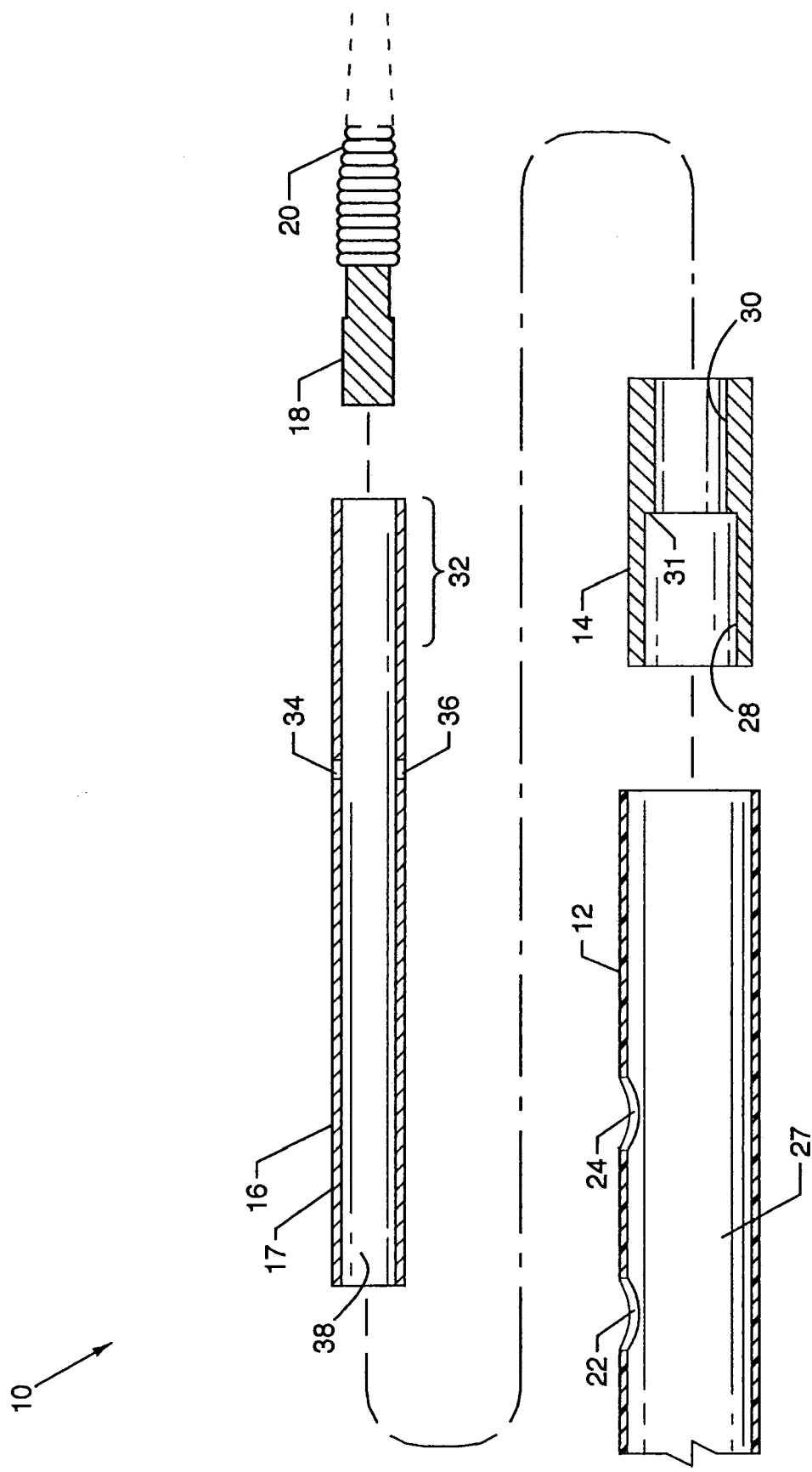
FIG. 3 is an exploded view in cross section of the miniature cross stream thrombectomy catheter along line 3-3 of FIG. 2.

FIG. 2 is an exploded isometric view of the miniature cross stream thrombectomy catheter 9, and FIG. 3 is an exploded cross section view along line 3-3 of FIG. 2 of the miniature cross stream thrombectomy catheter 10. With reference to FIGS. 2 and 3, further structure and features of the first embodiment of the instant invention are now described. The exhaust tube 12 includes an exhaust lumen 27 for proximally directed effluent flow of macerated thrombotic deposits, plaque, or other debris particles, as well as saline or other fluids, for collection, such as by a proximally located and connected manifold having exhaust means. The exhaust lumen 27 also provides a convenient conduit for the routing of the hypo-tube 16 which can connect to a high pressure saline source preferably through a manifold. The tubular flow director 14 aligns and suitably secures within the distal end of the lumen 27 of the exhaust tube 12 and includes a proximally located flow director bore 28 made continuous by a connecting annular transition 31 with a distally located flow director bore 30 where the distally located flow director bore 30 is of a lesser radius than the proximally located flow director bore 28, where each bore extends concentrically along the combined centerline of the flow director 14. The hypo-tube 16 aligns generally along the centerline of the exhaust tube 12, as well as aligning coaxially within the flow director bore 28 and flow director bore 30, and extends to form the hypo-tube extension 32 extending beyond the distal ends of the exhaust tube 12 and the flow director 14, as shown in FIG. 1. The hypo-tube 16 includes a lumen 38 extending the length of the hypo-tube 16 including extending along the hypo-tube extension 32 whereabout the plug 18 terminates the lumen 38. The hypo-tube extension 32, including the distal portion of the lumen 38, provides structure for accommodated mounting of the plug 18 therewithin. The plug 18 is secured therein, such as by a weldment, crimping, adhesive or other suitable method. One or more jet orifices extending through the wall of the hypo-tube 16 can be opposingly or otherwise suitably located proximal to the hypo-tube extension 32 of the hypo-tube 16. The example illustrated in FIG. 2 includes jet orifices 34 and 36.

Figure 4:
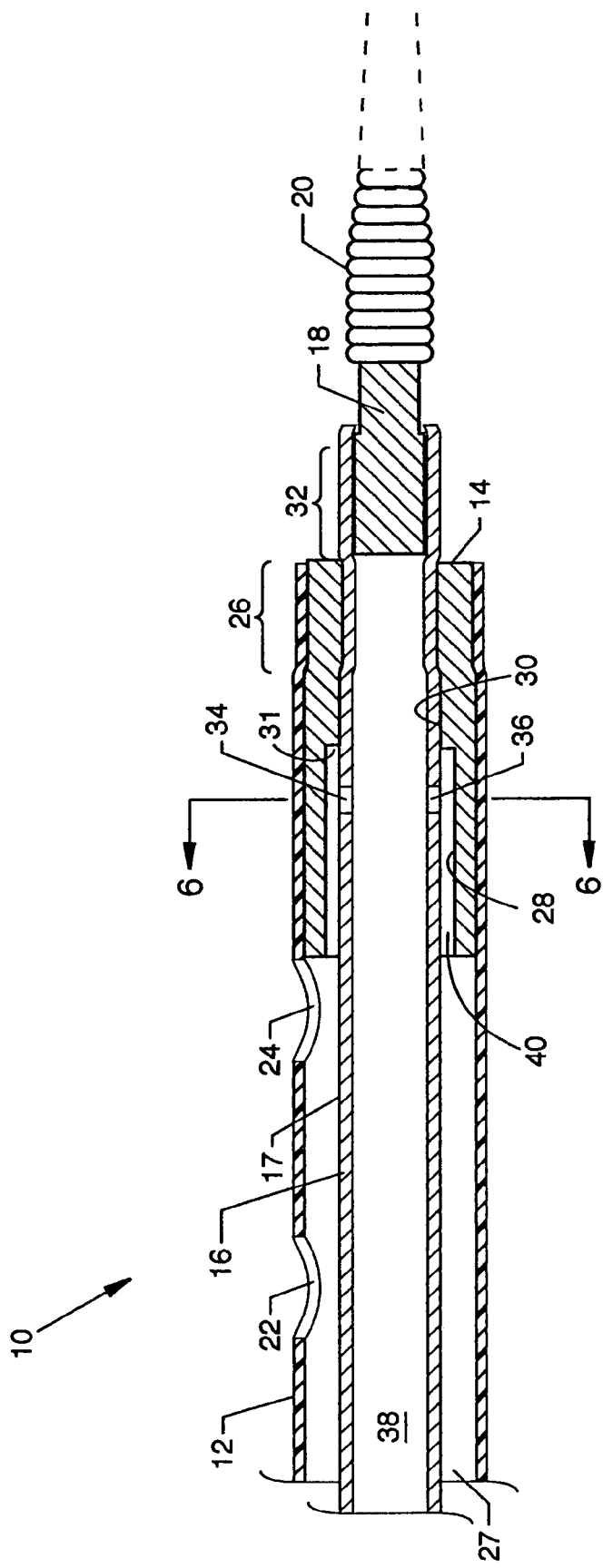
FIG. 4 is an assembled view in cross section of the components of FIG. 3.

FIG. 4 is an assembled view in cross section of the components of FIG. 3. FIG. 4 shows the relationship of the flow director 14, especially the proximally located flow director bore 28, to the immediate surrounding region of the hypo-tube 16 around and about the region having the jet orifices 34 and 36 and immediately proximal of the jet orifices 34 and 36 where an annulus 40 is formed between the proximally located flow director bore 28 and the outer surface 17 of the hypo-tube 16. The annulus 40 terminates at the annular transition 31 and is open to the exhaust lumen 27. The jet orifices 34 and 36 are communicatingly aligned in the distal region of the annulus 40 for best performance of the invention, as later described in detail. The crimp 26 at the distal end of the exhaust tube 12 causes frictional and mutual engagement and sealing of the distal regions of the exhaust tube 12, the flow director 14, and the hypo-tube 16 by compression thereof. Referring to FIGS. 1-4, the invention also includes a method of fabrication of a fluid jet catheter 10. The method includes providing a hypo-tube 16 with at least one jet orifice 34, 36, providing a plug 18 and inserting the plug 18 into the distal end of the hypo-tube 16, providing a flow director 14 and aligning the flow director 14 to the outside of the hypo-tube 16, providing an exhaust tube 12, inserting the hypo-tube 16 and flow director 14 into the exhaust tube 12 and aligning at a desired location in the exhaust tube 12, and crimping to provide engagement and sealing of the hypo-tube 16 and flow director 14 and exhaust tube 12.

Mode of Operation

Figure 5:
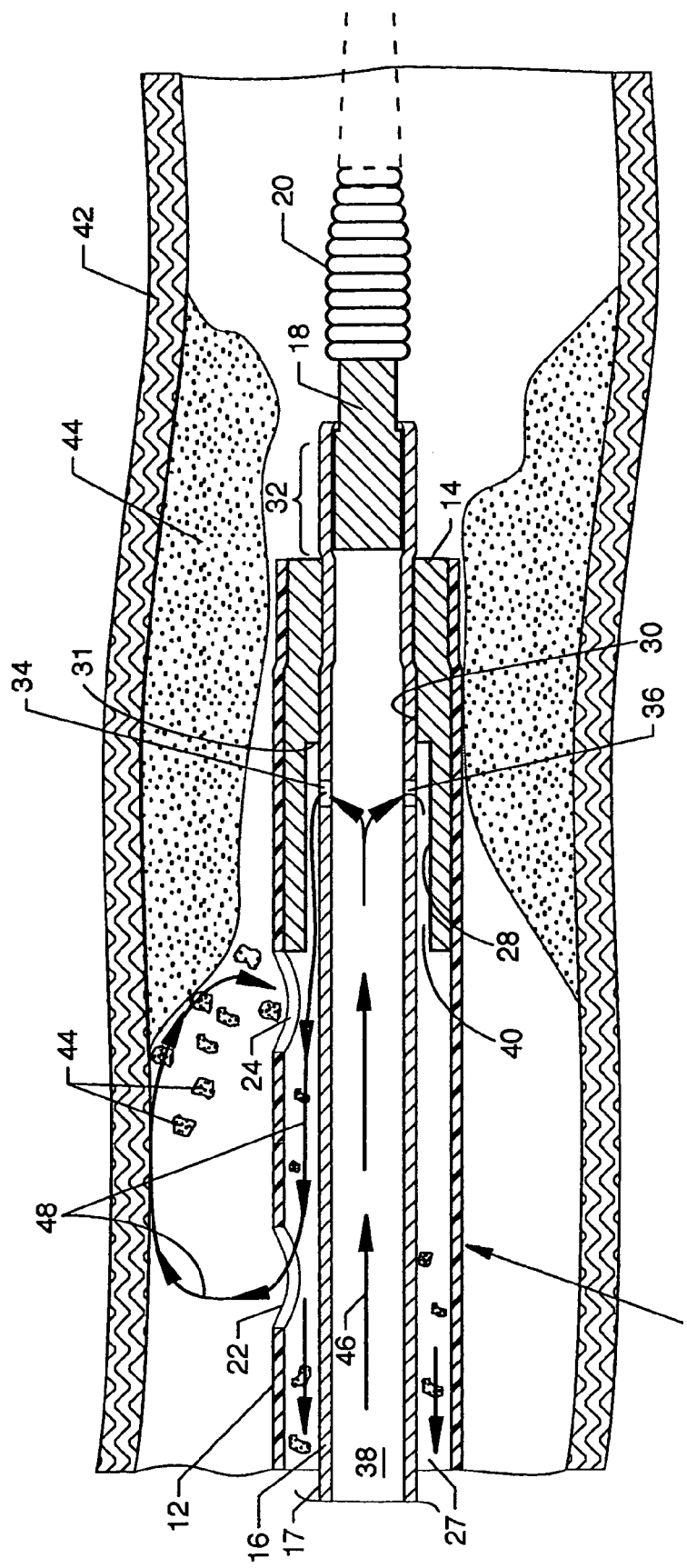
FIG. 5 is a cross section view of the miniature cross stream thrombectomy catheter showing the mode of operation where the distal end of an exhaust tube is positioned in a blood vessel at the site of a thrombotic deposit or lesion.
Figure 6:
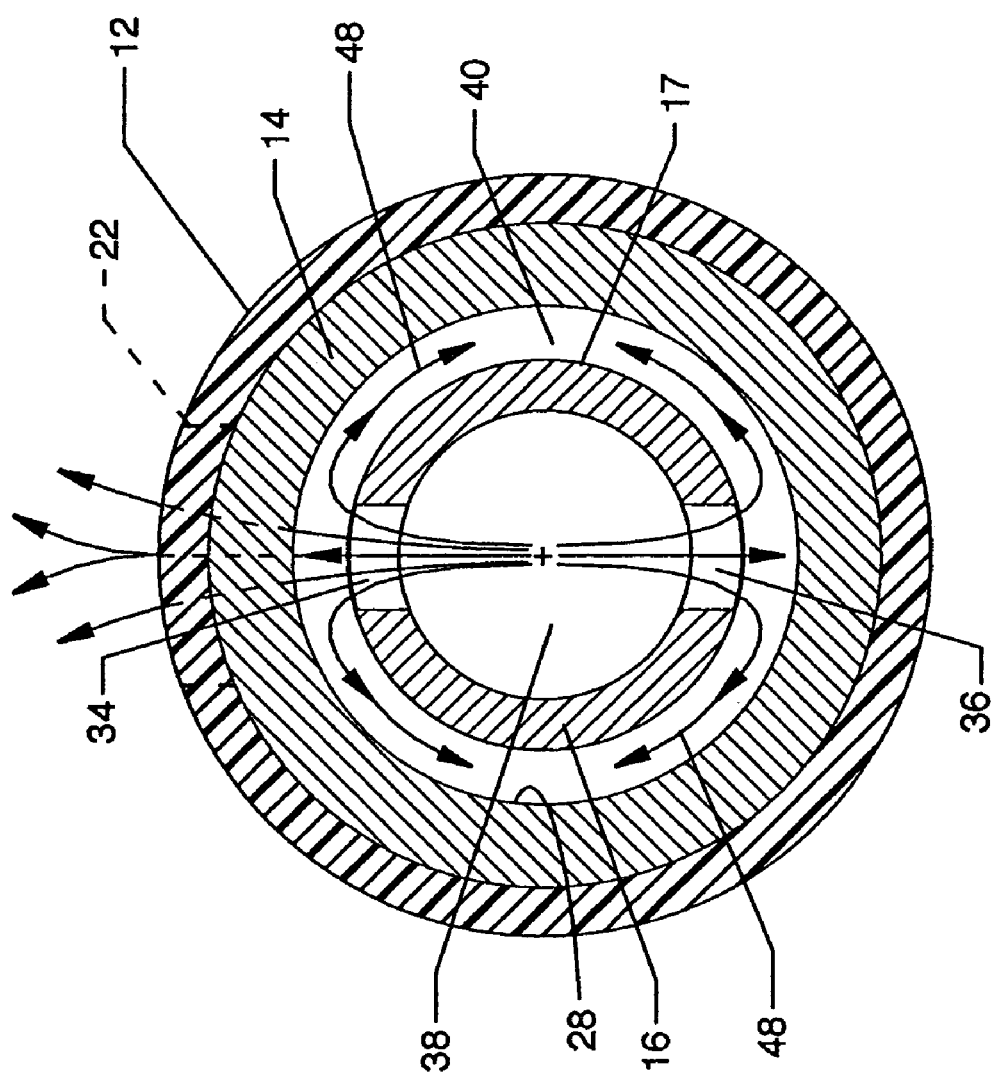
FIG. 6 is a cross section view along line 6-6 of FIG. 4 showing the flow of fluid jets along and about the annulus.

FIG. 5 is a cross section view of the miniature cross stream thrombectomy catheter 10 with particular attention given to the distal end of the exhaust tube 12 positioned in a blood vessel 42 at the site of a thrombotic deposit or lesion 44. FIG. 6 is a cross section view of the miniature cross stream thrombectomy catheter 10 along line 6-6 of FIG. 4 showing the relationship of the jet orifices 34 and 36, the annulus 40 surrounding the jet orifices 34 and 36 at the distal region of the hypo-tube 16, the outflow orifice 22, and the cross stream flow therewithin. With reference to FIGS. 5 and 6, the mode of operation is now described. FIG. 5 illustrates high pressure saline flow 46 from external high pressure supplies directed distally along and within the lumen 38 of the hypo-tube 16 to emanate from the jet orifices 34 and 36 as fluid jets 48 of saline of nominal and sufficient velocity, shown in path form. The fluid jets 48 traverse the annulus 40 in proximal redirection around, about and through the annulus 40, as also shown in FIG. 6. Fluid jet 48 flow is directed past the inflow orifice 24 thereby entraining and urging fluid and thrombus lesion debris through inflow orifice 24 and continuing in a proximal direction to outflow orifice 22, whereupon some of the fluid jet and entrained fluid and thrombus lesion debris passes through the outflow orifice 22 forming cross stream jets in a radial direction toward the wall of the blood vessel 42 where the fluid jets 48, at the same time, are influenced by the low pressure presented at the inflow orifice 24 by the rapid movement of the fluid jets 48, thereby causing the fluid jets 48 to flow circumferentially and distally to impinge and break up thrombotic deposits or lesions 44 and by entrainment to urge and carry along the thrombotic deposits or lesions 44 in particulate form through the inflow orifice 24, a relatively low pressure region, and into the exhaust lumen 27. The entrainment of broken-up thrombotic deposit or lesion 44 particulate through the inflow orifice 24 is based on entrainment by the fluid jets 48. The outflow through the exhaust lumen 27 is driven by internal pressure which is created by the remaining portion of the fluid jets 48 and entrained fluid and thrombus debris passing proximally along and between the outer surface 17 of the hypo-tube 16 and the exhaust lumen 27. Clot removal is enhanced by the recirculation pattern established between outflow and inflow orifices 22 and 24, respectively, which creates a flow field that maximizes drag force on wall-adhered thrombus. Note that while the path indicating fluid jets 48 on FIGS. 5 and 6 is shown following the annular space 40, and following the recirculation at outflow orifice 22 and inflow orifice 24 and therebetween, and following the exhaust lumen 27 proximal of outflow orifice 22, the constituents of the flow at various points along the paths of the fluid jets 48 are not identical. In annular space 40, jet flow indicated is essentially completely comprised of high pressure saline flow 46 which has passed through jet orifices 34 and 36 and may include some fluid entrained from annular space 40. As the jet flow passes inflow orifice 24, blood and thrombus debris is entrained with and mixes with the jet flow, so that the fluid in the recirculation flow includes saline plus entrained blood and thrombus debris. Therefore, the cross stream jet includes saline and blood and thrombus debris. Similarly, the flow along exhaust lumen 27 also includes saline and blood and thrombus debris. Thus, while a single designation of a fluid jet 48 is used, the fluid composition varies along the paths due to entrainment and mixing.

FIG. 6 is a cross section view along line 6-6 of FIG. 4 showing the flow of the fluid jets 48 along and about the annulus 40. Shown in particular is the flow of the fluid jets 48 which flow outwardly in radial fashion from the outflow orifices 34 and 36 and thence proximally and circumferentially, as shown in FIG. 5, and after mixing with fluid and thrombus debris entrained through inflow orifice 24, to exit through the outflow orifice 22 and then to flow distally to impinge, erode and otherwise break up thrombotic deposits or lesions 44 and thence to urge and carry broken-up thrombus or macerated thrombotic deposits or lesion particles to the inflow orifice 24 where the particles of thrombotic deposits or lesions 44 are further macerated and/or carried away through the exhaust lumen 27. Circumferential and distal flow occurs along and substantially parallel to the inner boundary of the blood vessel 42 in a direction leading to the inflow orifice 24, as shown in FIG. 5.

Figure 7:
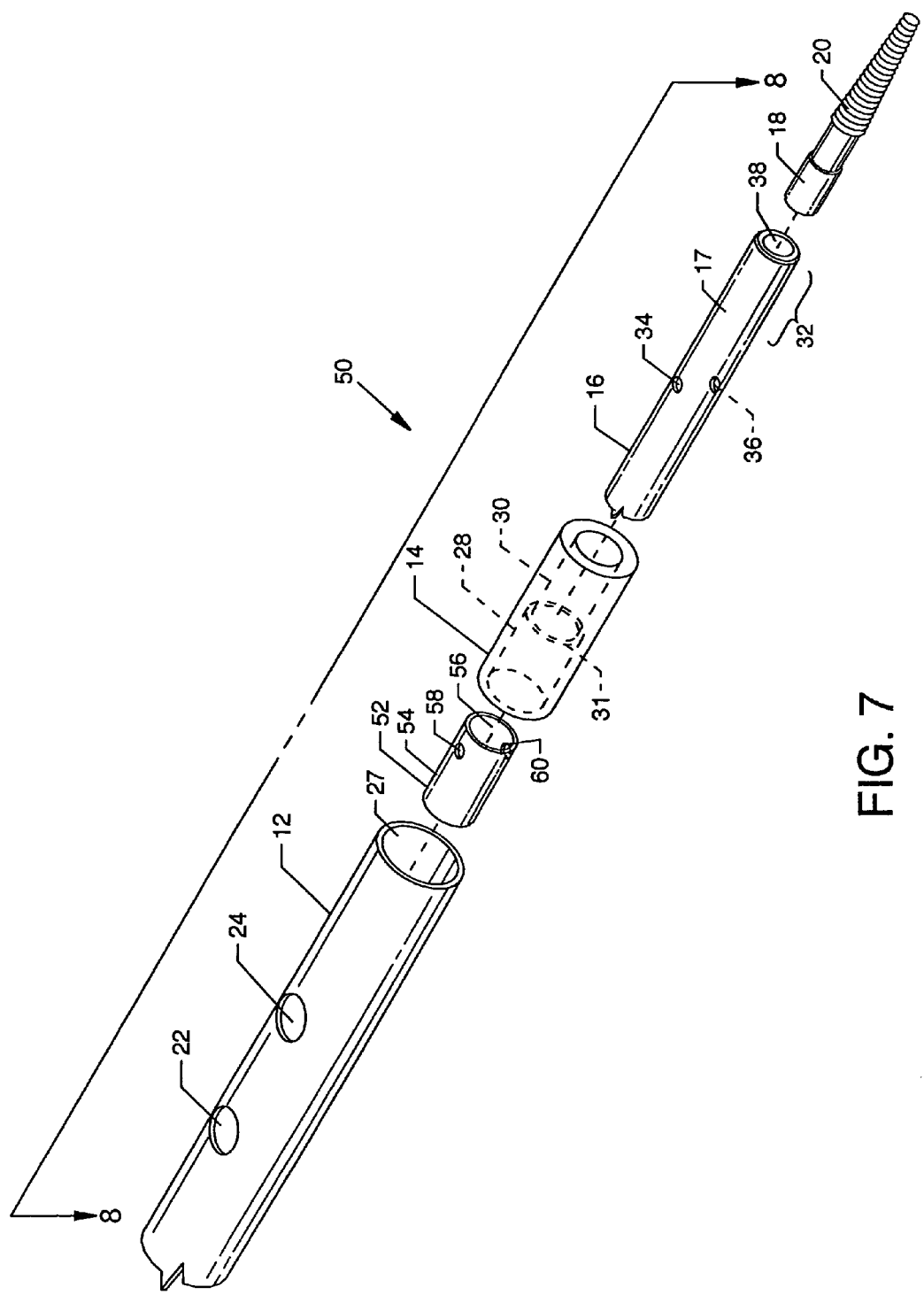
FIG. 7, a first alternative embodiment, is an exploded isometric view of a miniature cross stream thrombectomy catheter.
Figure 8:
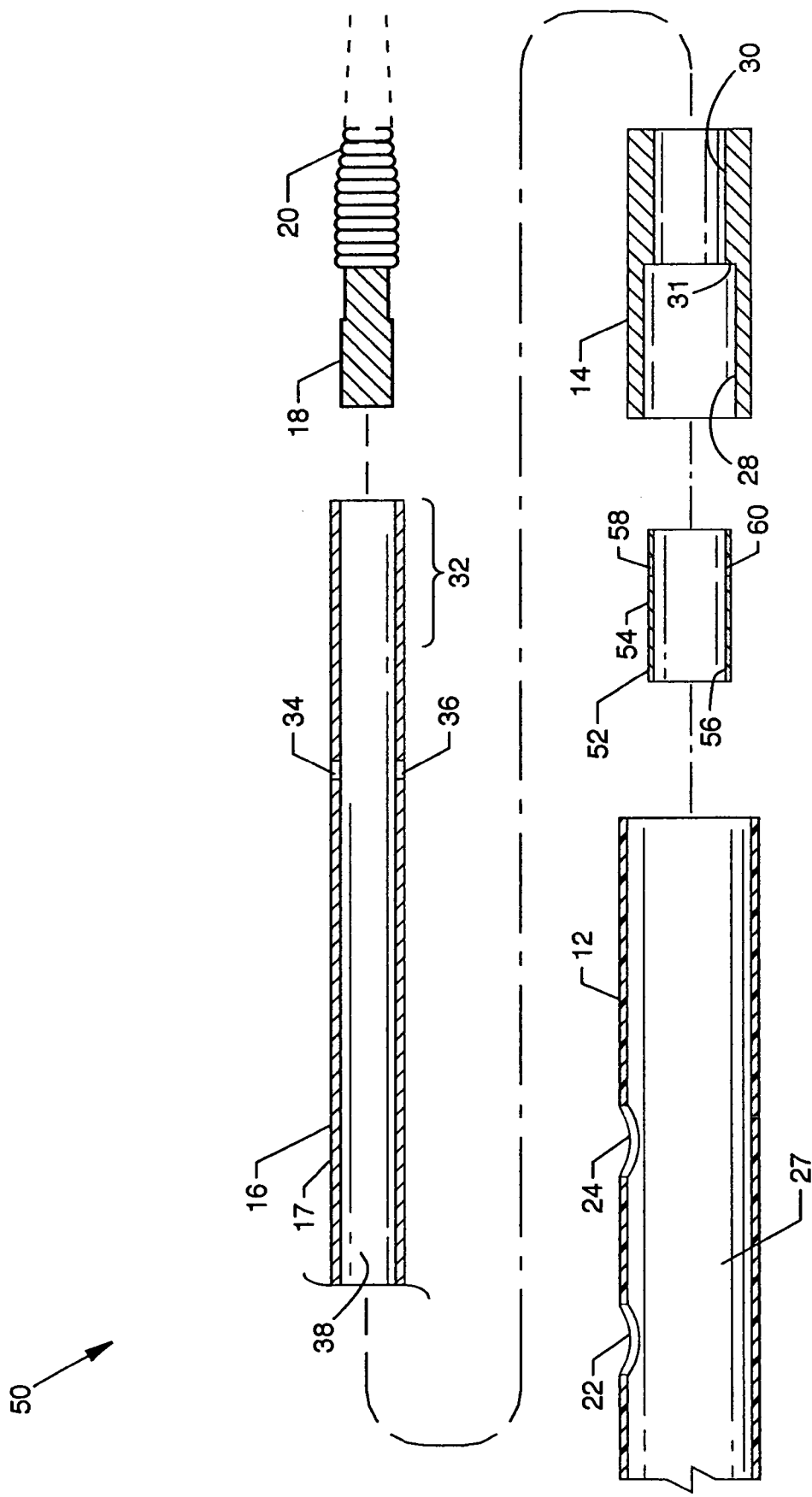
FIG. 8 is an exploded view in cross section of the miniature cross stream thrombectomy catheter of FIG. 7 along line 8-8 of FIG. 7.

FIG. 7, a first alternative embodiment, is an exploded isometric view of a miniature cross stream thrombectomy catheter 50 having the same external appearance as the miniature cross stream thrombectomy catheter 10. FIG. 8 is an exploded view in cross section of the miniature cross stream thrombectomy catheter 50. The miniature cross stream thrombectomy catheter 50 is comprised of the components previously described for the miniature cross stream thrombectomy catheter 10 but additionally includes a cylindrical-shaped insert 52. The insert 52 includes an outer surface 54, a bore 56 internal to the insert 52, and jet orifice extensions 58 and 60 extending from the outer surface 54 through the wall of the insert 52 to the bore 56. The relationship of the insert 52 to the hypo-tube 16 is such that the bore 56 of the insert 52 is sized to be closely fitted, accommodated by, and suitably secured to the outer surface 17 of the hypo-tube 16. The relationship of the insert 52 to the flow director 14 is such that the radius described by the outer surface 54 of the insert 52 is smaller than the radius of the proximally facing flow director bore 28 of the flow director 14 whereby the insert 52 aligns within the proximally located flow director bore 28 of the flow director 14. Such relationship is useful in formation of an alternately sized annulus 64 as viewed in FIG. 9.

Figure 9:
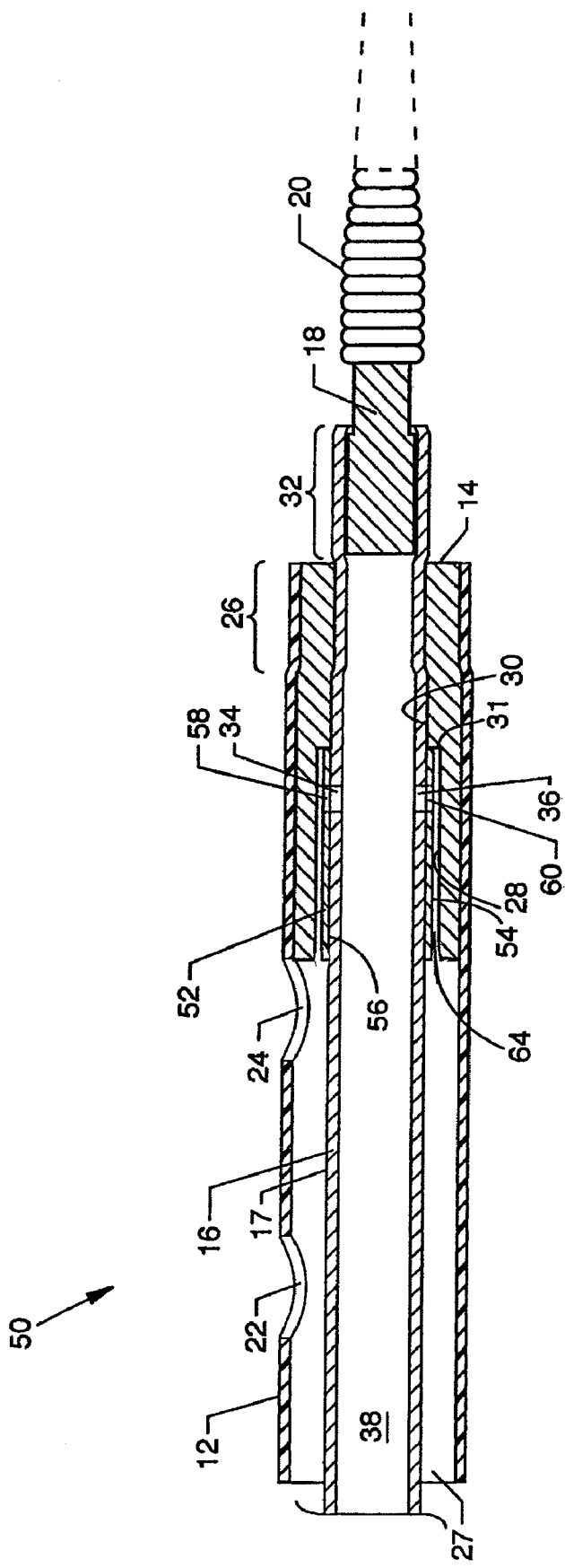
FIG. 9 is an assembled view in cross section of the components of FIG. 8.

FIG. 9 is an assembled view in cross section of the components of FIG. 8. FIG. 9 shows the relationship of the insert 52 co-located within the proximally located flow director bore 28 to the flow director bore 28, as well as the relationship of the insert 52 containing the opposed jet orifice extensions 58 and 60, which are opposingly or otherwise suitably located at the distal region of the insert 52, to the jet orifices 34 and 36 of the hypo-tube 16. Preferably, the jet orifice extensions 58 and 60 are in appropriate alignment with the jet orifices 34 and 36 of the hypo-tube 16, and preferably the distal end of the insert 52 abuts the annular transition 31 of the proximally facing flow director bore 28. The location of the insert 52 within the annulus formerly referred to as annulus 40 reduces the radial dimensions thereof to form an annulus 64 where the annulus 64 is of a thinner profile with respect to the profile of the annulus 40. The annulus 64 is formed by the proximally facing flow director bore 28 and the outer surface 54 of the insert 52. The annulus 64 terminates at the annular transition 31. Whereas the annulus 40 of the preceding first embodiment produced fluid jets 48 having a jet flow of useful and effective nominal velocity, the narrowed annulus 64 of the first alternative embodiment produces fluid jets 66 (FIG. 10), shown in path form, having a jet flow velocity greater than the nominal jet flow velocity of fluid jets 48 of the first embodiment and having greater velocity, thereby increasing the thrombus removal rate. Also, the inclusion of the insert 52 provides a fluid jet 66 flow path (FIG. 10) where the initial proximally directed flow is separated and offset from the hypo-tube 16, thereby reducing drag along the hypo-tube 16 to allow flow mostly unimpeded by contact with the hypo-tube 16. The combination of higher than nominal jet flow velocity with the reduction of drag along the hypo-tube 16 produces a powerful and highly effective flow for use in the general manner as previously described where the jet flow of the fluid jets 66 is incorporated substantially in the same manner with respect to creating an ablative flow exiting the outflow orifice 22 and re-entering the inflow orifice 24. The invention also includes a method of fabricating a fluid jet catheter, similar to the method disclosed for the first embodiment, but further comprising steps of providing an insert 52, aligning the insert to the hypo-tube 16 near the jet orifices 34, 36 and flow director 14, and affixing the insert 52 in the aligned position by frictional interference or by bonding.

Figure 10:
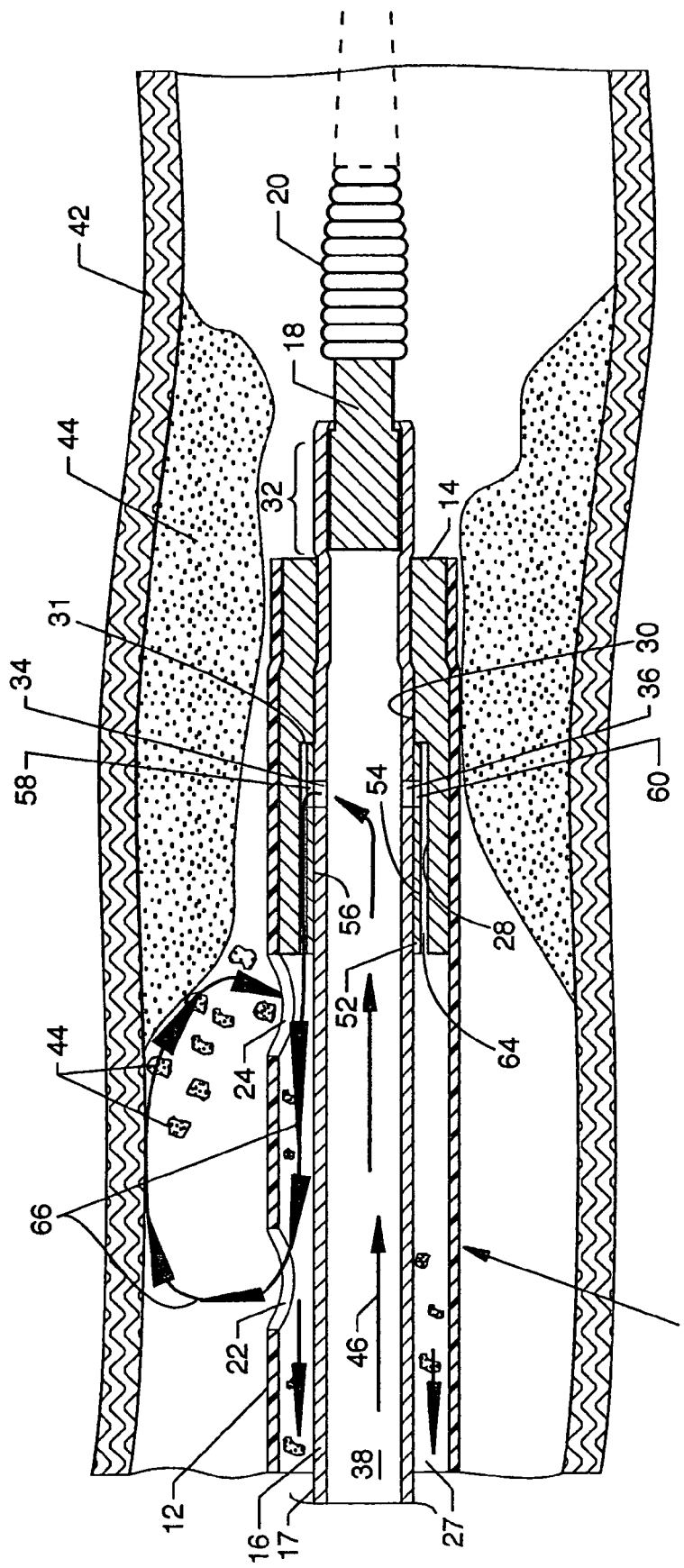
FIG. 10 is a cross section view of the miniature cross stream thrombectomy catheter of the first alternative embodiment showing the mode of operation where the distal end of an exhaust tube is positioned in a blood vessel at the site of a thrombotic deposit or lesion.

FIG. 10 is a cross section view of the miniature cross stream thrombectomy catheter 50, and shows the mode of operation with particular attention given to the distal end of the exhaust tube 12 positioned in a blood vessel 42 at the site of a thrombotic deposit or lesion 44. Operation of the miniature cross stream thrombectomy catheter 50 is generally similar to the operation of the miniature cross stream thrombectomy catheter 10 of the first embodiment; however, velocity increases of the jet flow of the fluid jets 66 and separation of flow from the hypo-tube 16 increase the effectiveness, the capability, and the speed of jet flows of the miniature cross stream thrombectomy catheter 50 with respect to the miniature cross stream thrombectomy catheter 9, the latter of which can be utilized where consideration is given to lessening the chances of vessel perforation by the use of nominal jet flow.

Figure 11:
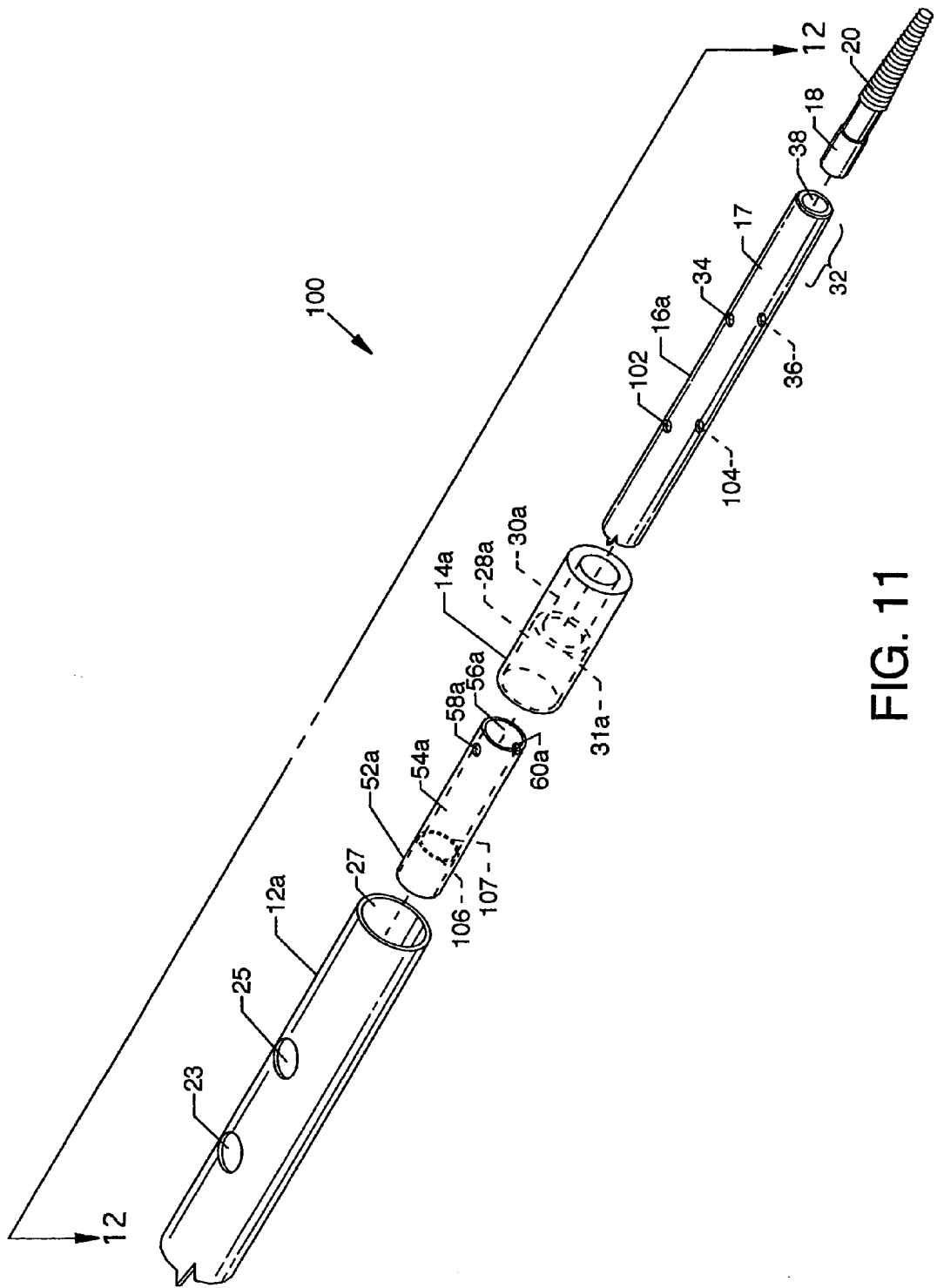
FIG. 11, a second alternative embodiment, is an exploded isometric view of a miniature cross stream thrombectomy catheter having more than one annulus.
Figure 12:
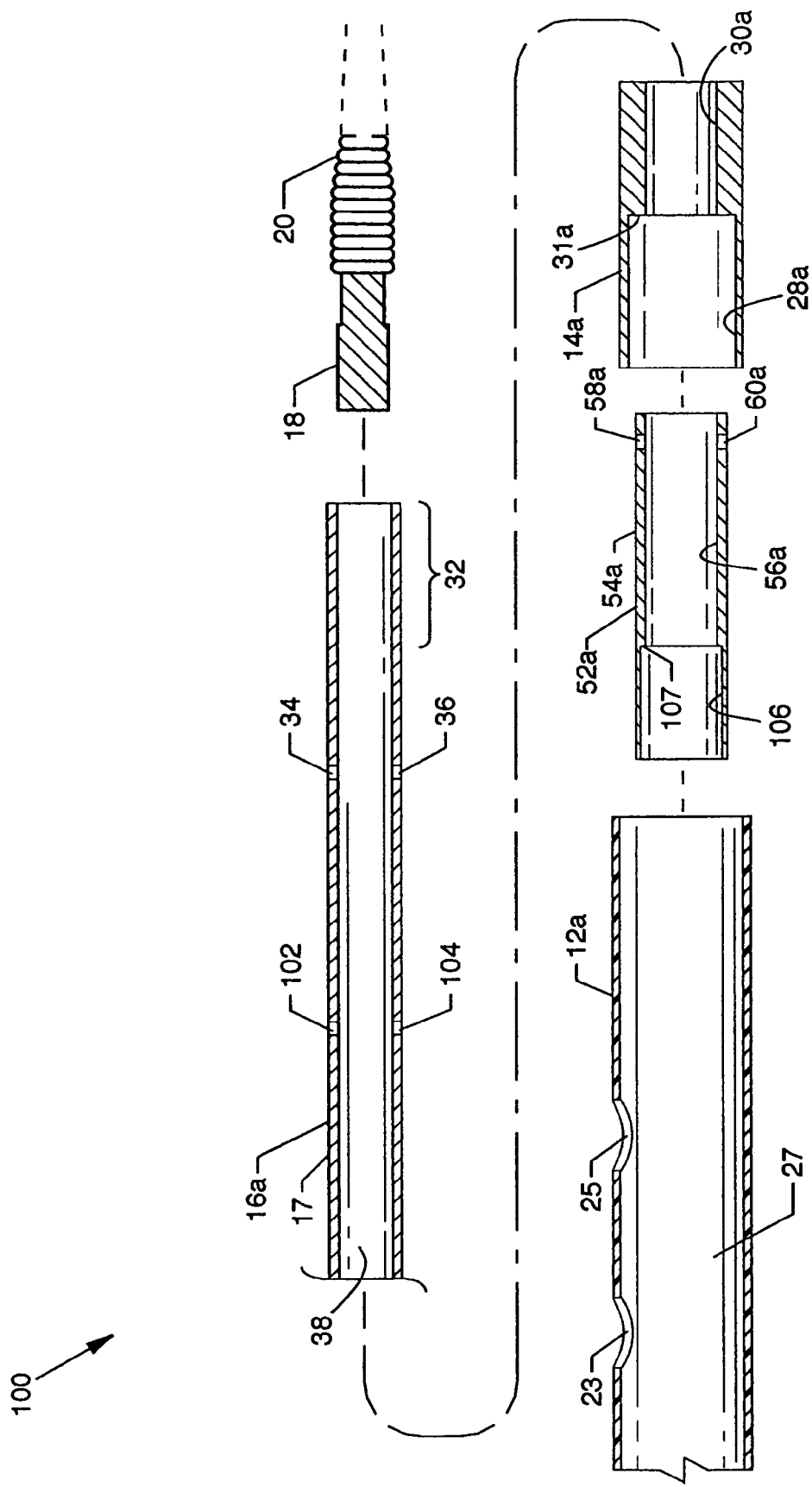
FIG. 12 is an exploded view in cross section of the miniature cross stream thrombectomy catheter of FIG. 11 along line 12-12 of FIG. 11.

FIG. 11, a second alternative embodiment, is an exploded isometric view of a miniature cross stream thrombectomy catheter 100 having more than one annulus and having the same external appearance as the miniature cross stream thrombectomy catheters 10 and 50. FIG. 12 is an exploded view in cross section of the miniature cross stream thrombectomy catheter 100. The miniature cross stream thrombectomy catheter 100 is comprised of components previously described or variations or modifications of previously described components for the miniature cross stream thrombectomy catheters 10 and 50 including an exhaust tube 12a, similar in many respects to the exhaust tube 12 shown in the first embodiment and first alternative embodiment, but where the previously shown outflow orifice 22 has been redesignated as an inflow orifice 23 and the previously shown inflow orifice 24 has been redesignated as an outflow orifice 25, an elongated cylindrical-shaped insert 52a similar in many respects to the cylindrical-shaped insert 52 shown in the first alternative embodiment, a hypo-tube 16a similar in many respects to the hypo-tube 16 shown in the first embodiment and first alternative embodiment, and a flow director 14a similar in many respects to the flow director 14 shown in the first embodiment and first alternative embodiment. The miniature cross stream thrombectomy catheter 100 includes features which offer low nominal velocity cross stream flow for thrombus ablation in delicate regions of blood vessels and which offer greater than nominal high velocity flow for removal of loosened and macerated thrombus along the exhaust lumen 27 of the exhaust tube 12a.

Components having variations or modifications are now described. The hypo-tube 16a is similar to and includes in addition to the previously described features of the hypo-tube 16 one or more jet orifices including jet orifices 102 and 104 extending through the wall of the hypo-tube 16a and being opposingly or otherwise suitably located proximal to the jet orifices 34 and 36. The elongated cylindrical-shaped insert 52a is similar in many respects to the cylindrical-shaped insert 52 and includes like and corresponding features, some of differing size or proportion, but closely related to the features of the insert 52, including an outer surface 54a, a bore 56a continuous with an adjacent and proximally located larger bore 106, there being a connecting annular transition 107 therebetween, and jet orifice extensions 58a and 60a. The flow director 14a is similar in many respects to the flow director 14 and includes like and corresponding features, some of differing size or proportion, but closely related to the features of the flow director 14, including a proximally located flow director bore 28a and a distally located flow director bore 30a and an annular transition 31a.

Figure 13:
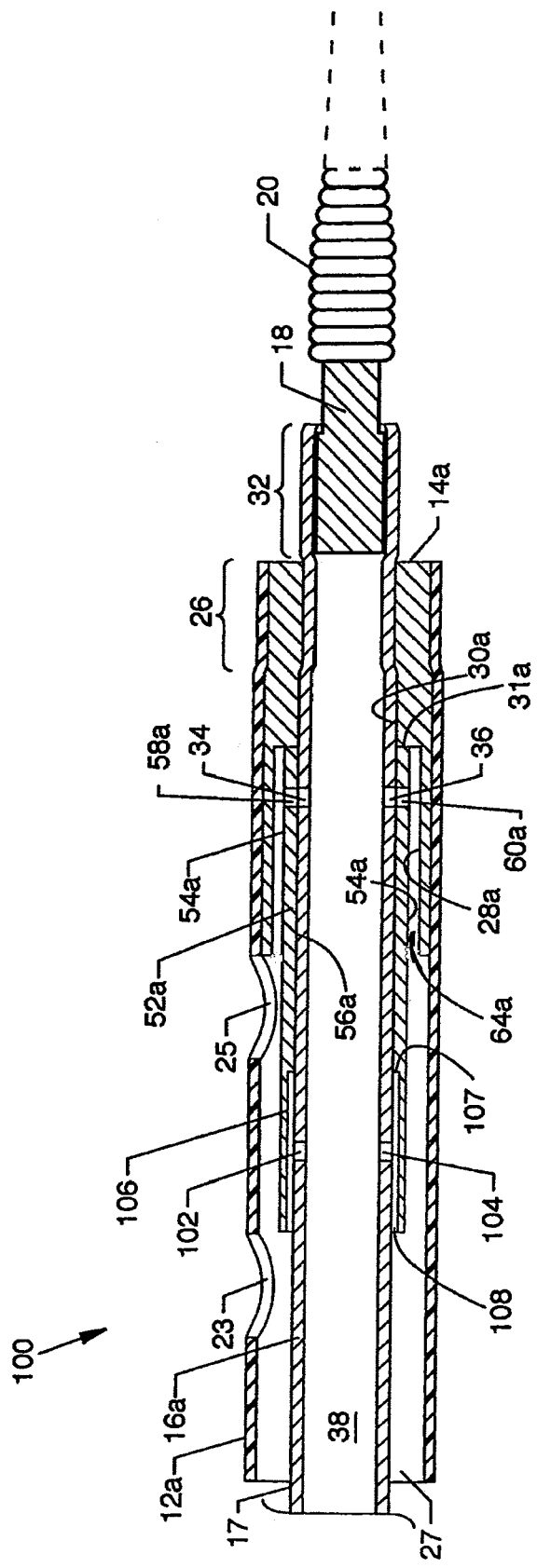
FIG. 13 is an assembled view in cross section of the components of FIG. 12.

FIG. 13 is an assembled view in cross section of the components of FIG. 12 where multiple annulus structure is formed. FIG. 13 shows the relationship of the elongated insert 52a co-located partially within the proximally located flow director bore 28a and extending proximally therefrom to be also partially located within and along the co-located region of the exhaust lumen 27 and the hypo-tube 16 and along and about the location of the outflow orifice 25 and the inflow orifice 23. The position of the elongated insert 52a as described forms an annulus 64a of distal location between the flow director bore 28a and the portion of the outer surface 54a of the elongated insert 52a opposing the proximally facing flow director bore 28a, and also forms an annulus 108 of proximal location between the bore 106 of the elongated insert 52a and the region of the outer surface 17 of the hypo-tube 16a opposing the bore 106 of the elongated insert 52a. The annulus 64a terminates at the annular transition 31a and the annulus 108 terminates at the annular transition 107.

Also shown is the relationship of the elongated insert 52a to the region of the hypo-tube 16a containing the opposed jet orifice extensions 58a and 60a opposingly or otherwise suitably located at the distal region of the insert 52a. Preferably, the jet orifice extensions 58a and 60a are in appropriate alignment with the jet orifices 34 and 36 of the hypo-tube 16a, and preferably the distal end of the insert 52a abuts the annular transition 31a of the proximally facing flow director bore 28a. The relationship of the jet orifices 102 and 104 to the annulus 108 is shown where the jet orifices 102 and 104 communicate between lumen 38 of the hypo-tube 16a and the annulus 108. The invention also includes a method of fabricating a fluid jet catheter, similar to the method disclosed for the first embodiment, but further comprising steps of providing at least one additional jet orifice 102, 104 in the hypo-tube 16a proximal to the first jet orifice(s) 34, 36, providing an elongated insert 52a, aligning the elongated insert 52a to the hypo-tube 16a near the jet orifices 102, 104 and flow director 14a to create additional flow direction for the additional jet orifice(s) 102, 104, and affixing the elongated insert 52a in the aligned position by frictional interference or by bonding.

Figure 14:
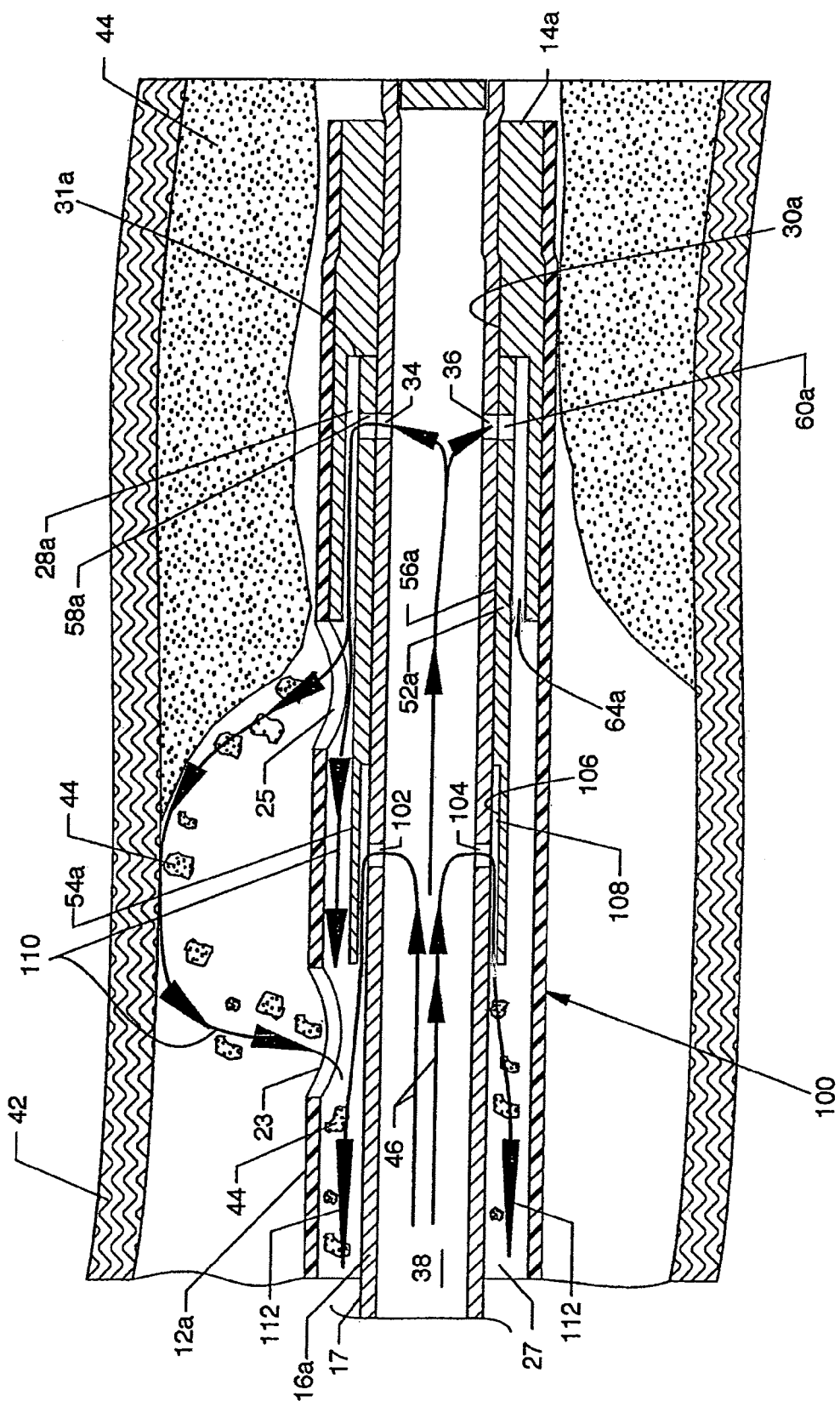
FIG. 14 is a cross section view of the miniature cross stream thrombectomy catheter of the second alternative embodiment showing the mode of operation where the distal end of an exhaust tube is positioned in a blood vessel at the site of a thrombotic deposit or lesion.

With reference to FIG. 14, the mode of operation of the second alternative embodiment is now described. FIG. 14 is a cross section view of the miniature cross stream thrombectomy catheter 100 with particular attention given to the distal end of the exhaust tube 12a positioned in a blood vessel 42 at the site of a thrombotic deposit or lesion 44. Multiple and substantially separate jet flows are generated at the distal region of the miniature cross stream thrombectomy catheter 100. One such flow of nominal force incorporates the major portion thereof to engage thrombotic deposits or lesions 44 and the like, whereby ablation occurs to erode, wear away, impinge and break up thrombotic deposits or lesions 44. Another flow of greater than nominal force is provided to readily and with great velocity urge broken-up thrombus 44 proximally for evacuation along the exhaust lumen 27 of the exhaust tube 12a.

High pressure saline flow 46 from external high pressure supplies is directed distally along and within the lumen 38 of the hypo-tube 16a to pass through the jet orifices 102 and 104 and to pass through the jet orifices 34 and 36 to create fluid jet flows.

High pressure saline flow 46 passing through the jet orifices 34 and 36 creates fluid jets 110 having jet flow paths following least resistance routes to traverse the annulus 64a in proximal redirection around, about and through the annulus 64a where the majority of the fluid jet flow created by the fluid jets 110 flows through the outflow orifice 25 and the balance of the fluid jet flow traverses along the exhaust lumen 27 of the exhaust tube 12a in a proximal direction first along and about the outer surface 54a of the elongated insert 52a and thence along and about the hypo-tube 16a, but being initially distanced by the outer surface 54a of the elongated insert 52a from the outside surface 17 of the hypo-tube 16a for drag reduction. After the majority of the fluid jet flow created by the fluid jets 110 flows through the outflow orifice 25, flow continues in a circuitous fashion and is utilized for ablative qualities to dislodge thrombotic deposits or lesions 44 and is influenced by the low pressure presented at the inflow orifice 23 to enter the lumen 27 of the exhaust tube 12a.

High pressure saline flow 46 passing through the jet orifices 102 and 104 creates fluid jets 112 having jet flow paths following least resistance routes to traverse the annulus 108 in proximal redirection around, about and through the annulus 108. The annulus 108 is of lesser cross section than the cross section of annulus 64a and, as such, offers an annulus 108 of more restrictive qualities with respect to the restrictive qualities of the larger cross section annulus 64a. Such restrictive qualities assist in proximal redirection of the jet flow paths of the fluid jets 112 to create a relatively high velocity and forceful proximally directed jet flow path for the purpose of evacuation of thrombotic particles 44 along the lumen 27 of the exhaust tube 12a. The fluid jets 112 created by flow through jet orifices 102 and 104 may thus have higher velocity than the fluid jets 110 created by flow through jet orifices 34 and 36, after redirection of the jets 112 and 110 by annulus 108 and annulus 64a, respectively. In addition, the jet flow 112 indicated proximally beyond the elongated insert 52a adds to and assists the generally directed proximal flow along the exhaust lumen 27. Thus, the higher velocity redirected jet flow from jet orifices 102 and 104 therefore aids in urging and propelling flow proximally along exhaust lumen 27 over and above the urging and propelling provided by redirected jet flow from jet orifices 34 and 36 and by any suction which may be applied to the proximal end of exhaust lumen 27.

Figure 15:
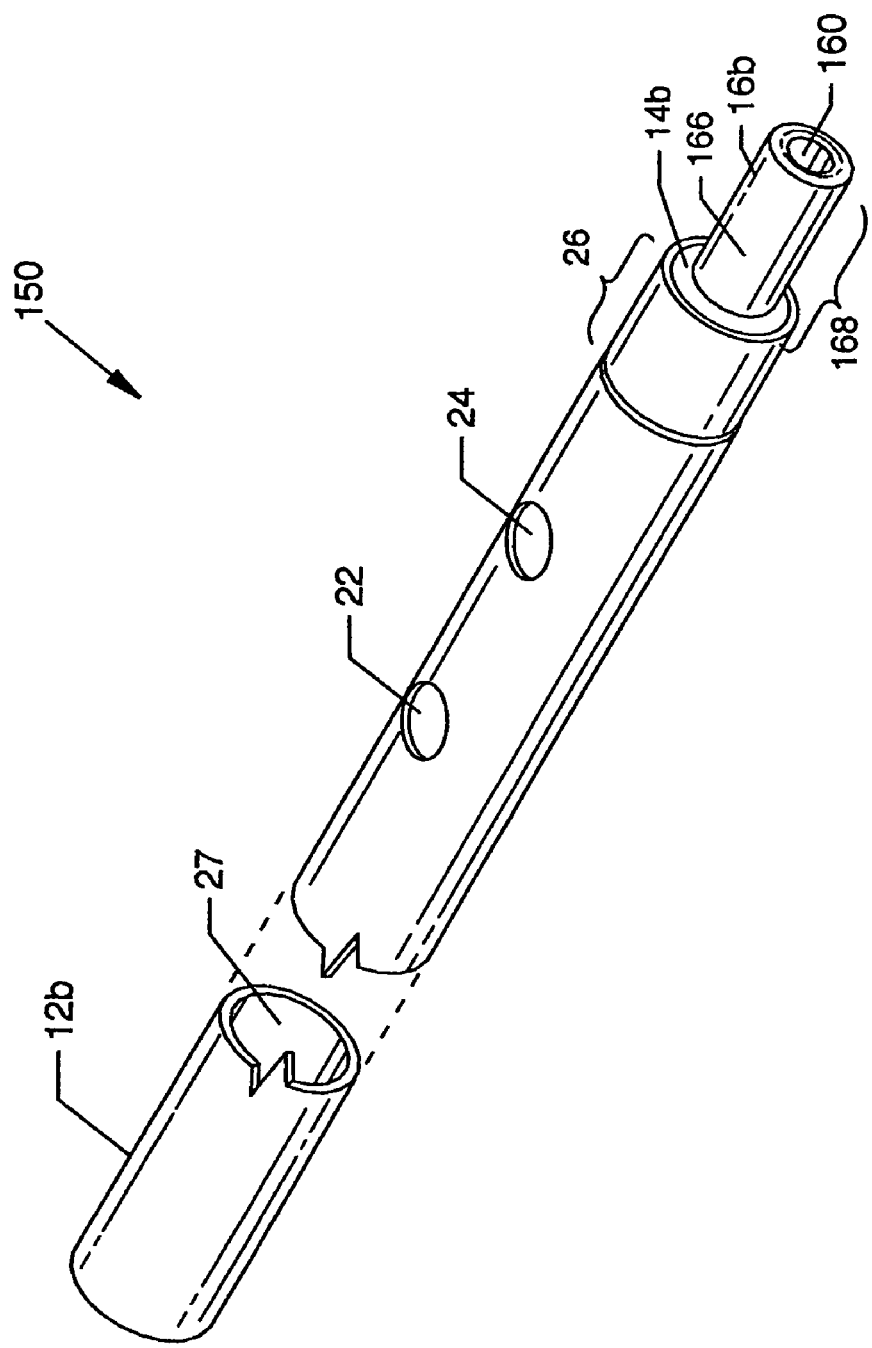
FIG. 15, a third alternative embodiment, is an isometric view of a miniature cross stream thrombectomy catheter for use over and about a guidewire.

FIG. 15, a third alternative embodiment, is an isometric view of a miniature cross stream thrombectomy catheter 150 which is for use over and about a guidewire and which is comprised of many of the components previously described or variations or modifications of previously described components used for the miniature cross stream thrombectomy catheter 50. In general, some of the main components can be of slightly larger dimension to accommodate a dual wall hypo-tube 16b, but the function of like components and structure of the device is similar to previously described corresponding component members. Readily viewed components of FIG. 15 include the exhaust tube 12b similar in many respects to the exhaust tube 12 which includes like and corresponding features, some of differing size or proportion, a flow director 14b similar in many respects to the flow director 14 which includes like and corresponding features, some of differing size or proportion, and a hypo-tube 16b having a dual wall, as later shown in detail, for accommodation of a guidewire.

Figure 16:
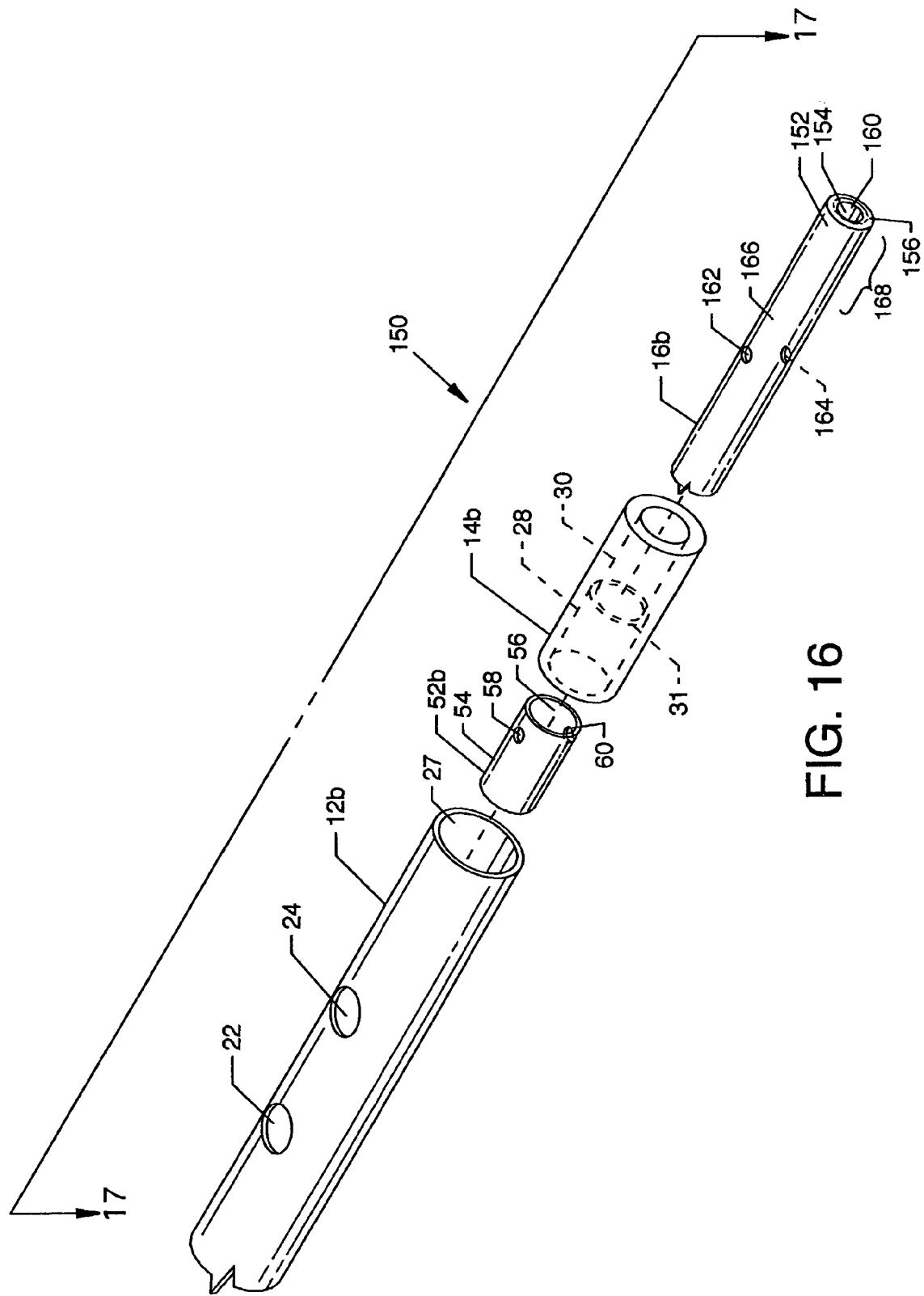
FIG. 16 is an exploded isometric view of the miniature cross stream thrombectomy catheter of FIG. 15.
Figure 17:
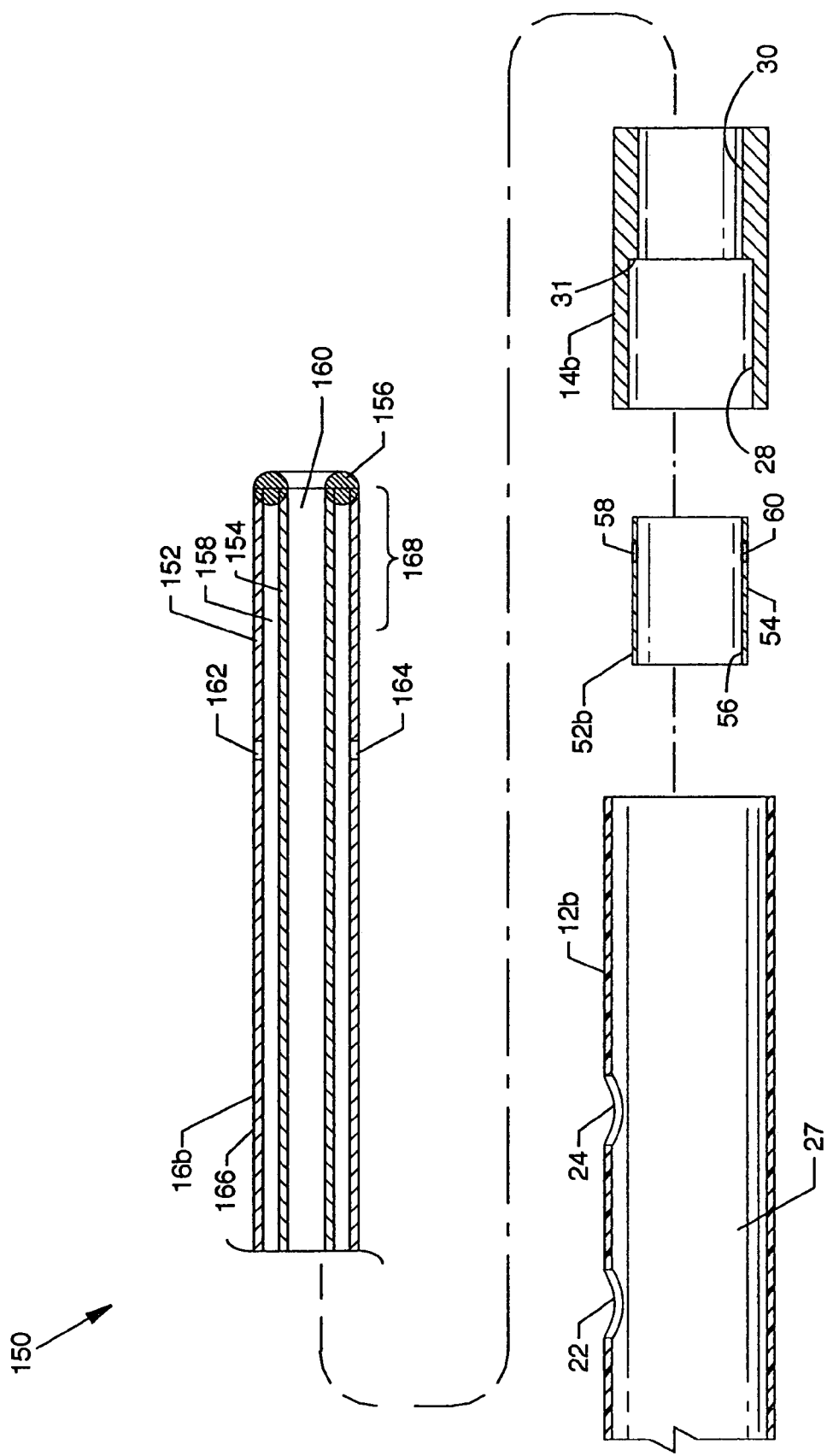
FIG. 17 is an exploded view in cross section of the miniature cross stream thrombectomy catheter of FIG. 16 along line 17-17 of FIG. 16; and, FIG. 18 is an assembled view in cross section of the components of FIG. 17 showing the relationship of the dual wall hypo-tube to the other components at the distal end of the miniature cross flow thrombectomy catheter.
Figure 18:
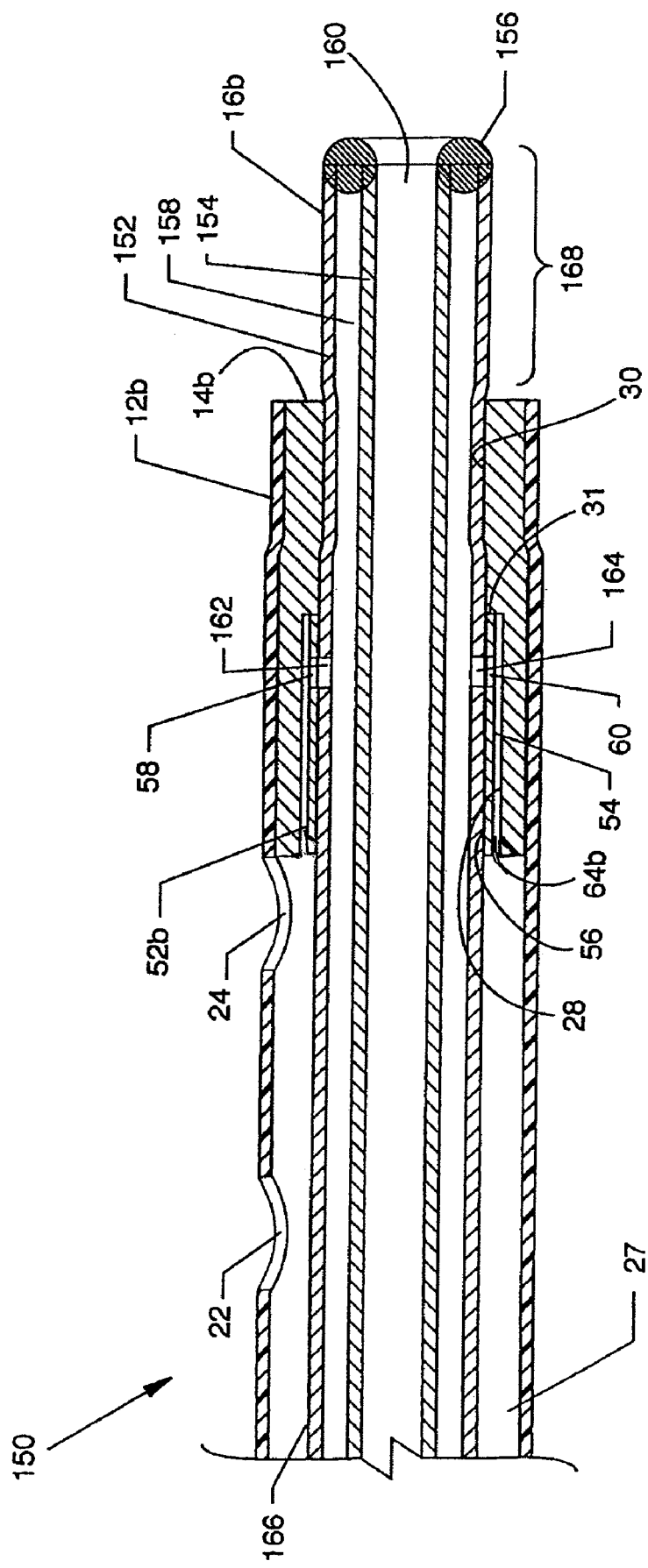

FIG. 16 is an exploded isometric view of the miniature cross stream thrombectomy catheter 150, and FIG. 17 is an exploded view in cross section of the miniature cross stream thrombectomy catheter 150 along line 17-17 of FIG. 16. The miniature cross stream thrombectomy catheter 150 includes the dual wall hypo-tube 16b and components previously described or variations or modifications of previously described components used for the miniature cross stream thrombectomy catheter 50. Also shown in FIGS. 16 and 17 is an insert 52b similar in many respects to the insert 52 of the miniature cross stream thrombectomy catheter 50 and which includes like and corresponding features, some of differing size or proportion. The dual wall hypo-tube 16b includes an outer wall 152 spaced concentrically over and about an inner wall 154, an annular lumen 158 (FIG. 17) formed between the outer wall 152 and the inner wall 154 for accommodation of pressurized saline flow, a seal 156, which can be a weld or other suitable structure, sealing the distal ends of the outer wall 152 and the inner wall 154, and a suitable seal and high pressure saline input port (not shown) at the proximal ends of the outer wall 152 and inner wall 154. A passageway 160 is formed by the inner wall 154 for accommodation over and about a guidewire. Jet orifices 162 and 164, which can be opposingly or otherwise suitably located, extend through the outer wall 152 in common with and to communicate with the annular lumen 158 in order to produce fluid jets in the same manner as shown in FIG. 10. The dual wall hypo-tube 16b also includes an outer surface 166 which closely aligns within the distally facing flow director bore 30 and which aligns in other components, as shown in FIG. 18. A hypo-tube extension 168 at the distal portion of the dual wall hypo-tube 16b extends beyond the distal ends of the flow director 14b and the exhaust tube 12b, as viewed in FIG. 15.

FIG. 18 is an assembled view in cross section of the components of FIG. 17 showing the relationship of the dual wall hypo-tube 16b to the other components at the distal end of the miniature cross stream thrombectomy catheter 150. Shown in particular is the annulus 64b formed between the proximally facing flow director bore 28 and the outer surface 54 of the insert 52b. The annulus 64b is in communication with the annular lumen 158 via the jet orifice extensions 58 and 60 and the respective aligned jet orifices 162 and 164. With the exception of the inclusion of the dual wall hypo-tube 166 for accommodation of a guidewire, operation of the miniature cross flow thrombectomy catheter 150 is the same as described for the miniature cross flow thrombectomy catheter 50. The invention includes a method of fabricating a dual wall hypo-tube 16b comprising the steps of providing an outer wall 152 having fluid jet orifice(s) 162, 164, providing an inner wall 154 of smaller diameter than the outer wall 152, passing the inner wall 154 coaxially within the outer wall 152, and forming a seal 156 between the distal ends of the outer wall 152 and the inner wall 154. The invention also includes a method of fabricating a fluid jet catheter, similar to the method disclosed for the first embodiment, but wherein the provided hypo-tube 16 is a dual wall hypo-tube 16a. An additional inventive method further includes the steps of providing an insert 52b, aligning the insert 52b to the hypo-tube 16a near the jet orifices 162,164 and flow director 14b, and affixing the insert 52b in the aligned position by frictional interference or by bonding. The outer wall 152 and the inner wall 154 can comprise hypo-tubes.

Various modifications can be made to the present invention without departing from the apparent scope thereof.

MINIATURE CROSS STREAM THROMBECTOMY CATHETER PARTS LIST

| | |
|---|---|
| 10 | miniature cross stream thrombectomy catheter |
| 12 | exhaust tube |
| 12a | exhaust tube |
| 12b | exhaust tube |
| 14 | flow director |
| 14a | flow director |
| 14b | flow director |
| 16 | hypo-tube |
| 16a | hypo-tube |
| 16b | dual wall hypo-tube |
| 17 | outer surface |
| 18 | plug |
| 20 | flexible tip |
| 22 | outflow orifice |
| 23 | inflow orifice |
| 24 | inflow orifice |
| 25 | outflow orifice |
| 26 | crimp |
| 27 | exhaust lumen |
| 28 | flow director bore (proximal) |
| 28a | flow director bore (proximal) |
| 30 | flow director bore (distal) |
| 30a | flow director bore (distal) |
| 31 | annular transition |
| 31a | annular transition |
| 32 | hypo-tube extension |
| 34 | jet orifice |
| 36 | jet orifice |
| 38 | lumen (hypo-tube) |
| 40 | annulus |
| 42 | blood vessel |
| 44 | thrombotic deposit or lesion |
| 46 | high pressure saline flow |
| 48 | fluid jets |
| 50 | miniature cross stream thrombectomy catheter |
| 52 | insert |
| 52a | elongated insert |
| 52b | insert |
| 54 | outer surface |
| 54a | outer surface |
| 56 | bore (insert) |
| 56a | bore (insert) |
| 58 | jet orifice extension |
| 58a | jet orifice extension |
| 60 | jet orifice extension |
| 60a | jet orifice extension |
| 64 | annulus |
| 64a | annulus |
| 64b | annulus |
| 66 | fluid jets |
| 100 | miniature cross stream thrombectomy catheter |
| 102 | jet orifice |
| 104 | jet orifice |
| 106 | bore |
| 107 | annular transition |
| 108 | annulus |
| 110 | fluid jets |
| 112 | fluid jets |
| 150 | miniature cross stream thrombectomy catheter |
| 152 | outer wall |
| 154 | inner wall |
| 156 | seal |
| 158 | annular lumen |
| 160 | passageway |
| 162 | jet orifice |
| 164 | jet orifice |
| 166 | outer surface |
| 168 | hypo-tube extension |

It is claimed:

1. A fluid jet catheter for removal of unwanted material from a body vessel or cavity comprising;
   a. a hypo-tube having a proximal end and a distal end and a wall, said hypo-tube configured for passage of high pressure fluid from said proximal end to said distal end, said hypo-tube having at least two jet orifices in said wall near said distal end for creation of at least two high velocity fluid jets;
b. a plug configured to seal the distal end of said hypo-tube;
c. a flow director having a proximal region and a distal region oriented to redirect said at least two high velocity fluid jets in a proximal direction;
d. an exhaust tube for removal of fluid and unwanted material, said exhaust tube having a distal region, at least one inflow orifice and at least one outflow orifice;
e. said hypo-tube having an extended hypo-tube portion having a distal region which extends distally past said flow director; and,
f. a crimp which provides engagement and sealing of the distal regions of said exhaust tube and said flow director and said extended hypo-tube portion wherein said crimp ensures alignment between the jet orifices of the hypo-tube and the proximal region of the flow director.

2. The fluid jet catheter of claim 1, wherein said flow director has an inside and an outside and is configured to fit closely to said hypo-tube on the inside and said exhaust tube on the outside, to provide for attachment and fluid sealing between said hypo-tube, said flow director, and said exhaust tube.

3. The fluid jet catheter of claim 1, further comprising a flexible tip secured about and extending from said plug.

4. The fluid jet catheter of claim 1, wherein said hypo-tube comprises a metallic tube.

5. The fluid jet catheter of claim 1, wherein said hypo-tube comprises a high-strength polymeric tube.

6. The fluid jet catheter of claim 1 wherein said exhaust tube comprises a flexible polymeric tube.

7. The fluid jet catheter of claim 1, wherein said at least two high velocity fluid jets are redirected by said flow director to pass in the vicinity of said at least one inflow orifice and provide entrainment of fluid and unwanted material from the blood vessel through said at least one inflow orifice and create a pressure to drive fluid through said at least one outflow orifice creating at least one cross stream jet.

8. The fluid jet catheter of claim 1, wherein said hypo-tube and said flow director are configured to form an annular space for fluid jet flow proximal from said at least two jet orifices.

9. The fluid jet catheter of claim 1 further comprising:
a. an insert configured to fit around said hypo-tube in the vicinity of said at least two jet orifices; and,
b. said insert having at least two orifice extensions aligned with said at least two jet orifices.

10. The fluid jet catheter of claim 9, wherein said insert is configured to provide separation of flow of said at least two fluid jets from said hypo-tube.

11. The fluid jet catheter of claim 9, wherein said insert is configured to form an annular space for fluid jet flow proximal from said at least two jet orifices, wherein said annular space is smaller than that which would exist without said insert.

12. The fluid jet catheter of claim 11, wherein said at least two high velocity fluid jets are redirected by said flow director to pass at a higher flow velocity than that which would occur without said insert in the vicinity of said at least one inflow orifice to provide enhanced entrainment of fluid and unwanted material from the blood vessel through said at least one inflow orifice and create a pressure to drive fluid through said at least one outflow orifice creating at least one cross stream jet.

13. The fluid jet catheter of claim 1, further comprising:
a. at least one additional orifice in said wall of said hypo-tube and located more proximal than said at least one jet orifice for creation of at least one additional fluid jet;
b. an insert configured to fit around said hypo-tube in the vicinity of said at least one jet orifice, and extended to form an additional flow director in the vicinity of said at least one additional orifice; and,
c. said insert having at least one orifice extension aligned with said at least one jet orifice.

14. The fluid jet catheter of claim 13, wherein:
a. said hypo-tube and said flow director are configured to form an annular space for fluid jet flow proximal from said at least one jet orifice;
b. said hypo-tube and said additional flow director are configured to form an additional annular space for fluid jet flow proximal from said at least one additional orifice; and,
c. said additional annular space with said additional orifice provides greater fluid flow velocity that said annular space with said at least one jet orifice.

15. The fluid jet catheter of claim 13, wherein said at least one high velocity fluid jet is redirected by said flow director to create at least one cross stream jet, and said at least one additional fluid jet is configured to urge fluid and unwanted material towards the proximal end of said exhaust tube.

* * * * *

UNITED STATES PATENT AND TRADEMARK OFFICE
CERTIFICATE OF CORRECTION

| | | |
|---|---|---|
| PATENT NO. | : 7,572,244 B2 | Page 1 of 1 |
| APPLICATION NO. | : 10/910108 | |
| DATED | : August 11, 2009 | |
| INVENTOR(S) | : Weisel et al. | |

It is certified that error appears in the above-identified patent and that said Letters Patent is hereby corrected as shown below:

In Column 4, Line 25, delete "9," and insert -- 10, --, therefor

In Column 4, Line 46, delete "9," and insert -- 10, --, therefor

In Column 8, Line 2, delete "9," and insert -- 10, --, therefor

Signed and Sealed this

Twenty-second Day of September, 2009

David J. Kappos
*Director of the United States Patent and Trademark Office*